(12) United States Patent
Beckers et al.

(10) Patent No.: US 10,350,273 B2
(45) Date of Patent: Jul. 16, 2019

(54) TREATMENT OF HORMONAL DISORDERS OF GROWTH

(71) Applicants: The United States of America, as represented by the Secretary, Department of Health and Human Services, Washington, DC (US); UNIVERSITE DE LIEGE, Angleur (BE); CENTRE HOSPITALIER UNIVERSITAIRE DE LIEGE, Liege (BE)

(72) Inventors: Albert Beckers, Pepinster (BE); Adrian Francis Daly, Gijon (ES); Fabio Rueda Faucz, Bethesda, MD (US); Constantine A. Stratakis, Bethesda, MD (US); Giampaolo Trivellin, Bethesda, MD (US)

(73) Assignees: The United States of America, as represented by the Secretary, Department of Health and Human Services, Washington, DC (US); Université de Liége and Centre Hospitalier Universitaire De Liége, Leige (BE)

( * ) Notice: Subject to any disclaimer, the term of this patent is extended or adjusted under 35 U.S.C. 154(b) by 0 days.

(21) Appl. No.: 15/525,928

(22) PCT Filed: Nov. 12, 2015

(86) PCT No.: PCT/US2015/060442
§ 371 (c)(1),
(2) Date: May 10, 2017

(87) PCT Pub. No.: WO2016/077620
PCT Pub. Date: May 19, 2016

(65) Prior Publication Data
US 2017/0304405 A1    Oct. 26, 2017

Related U.S. Application Data

(60) Provisional application No. 62/078,517, filed on Nov. 12, 2014.

(51) Int. Cl.
| | |
|---|---|
| *A61K 38/31* | (2006.01) |
| *C07K 14/705* | (2006.01) |
| *C12N 15/113* | (2010.01) |
| *A61K 31/713* | (2006.01) |
| *C07K 16/28* | (2006.01) |
| *A61K 38/12* | (2006.01) |
| *A61K 38/27* | (2006.01) |
| *A61K 47/60* | (2017.01) |
| *A61K 31/352* | (2006.01) |
| *A61K 31/437* | (2006.01) |
| *A61K 31/473* | (2006.01) |
| *A61K 38/17* | (2006.01) |
| *A61K 31/48* | (2006.01) |

(52) U.S. Cl.
CPC ............ *A61K 38/31* (2013.01); *A61K 31/352* (2013.01); *A61K 31/437* (2013.01); *A61K 31/473* (2013.01); *A61K 31/48* (2013.01); *A61K 31/713* (2013.01); *A61K 38/12* (2013.01); *A61K 38/1709* (2013.01); *A61K 38/27* (2013.01); *A61K 47/60* (2017.08); *C07K 14/705* (2013.01); *C07K 16/28* (2013.01); *C12N 15/1138* (2013.01); *C12N 2310/11* (2013.01); *C12N 2310/14* (2013.01)

(58) Field of Classification Search
CPC .............................. A61K 38/31; C07K 14/705
See application file for complete search history.

(56) References Cited

U.S. PATENT DOCUMENTS

| | | | | |
|---|---|---|---|---|
| 8,142,762 B2 * | 3/2012 | Bagnol | .................. | A61K 31/00 424/9.2 |
| 2010/0056442 A1 * | 3/2010 | Bagnol | .................. | A61K 31/00 514/1.1 |

FOREIGN PATENT DOCUMENTS

| | | |
|---|---|---|
| EP | 0137689 A1 | 4/1985 |
| WO | WO 2006/108667 A2 | 10/2006 |
| WO | WO 2012/068065 A2 | 5/2012 |

OTHER PUBLICATIONS

Lee et al., 2001, Discovery and mapping of ten novel G protein-coupled receptor genes, Gene, 275: 83-91.*

(Continued)

*Primary Examiner* — Amber D Steele
(74) *Attorney, Agent, or Firm* — Klarquist Sparkman LLP

(57) ABSTRACT

The present invention refers to a GPR101 inhibitor, antagonist or inverse agonist or inverse agonist for use in preventive and/or therapeutic treatment of diseases selected from the group consisting of acromegaly and gigantism and to methods for preventive and/or therapeutic treatment of diseases selected from the group consisting of acromegaly and gigantism. Further, the present invention provides a GPR101 agonist for use in preventive and/or therapeutic treatment of disorders selected from the group consisting of dwarfism, short stature, hypopituitarism and a disease of low levels of pituitary hormone secretion and to methods for preventive and/or therapeutic treatment of diseases selected from the group consisting of dwarfism, short stature, hypopituitarism and a disease of low levels of pituitary hormone secretion wherein to a subject GPR101 agonist is administered.

12 Claims, 7 Drawing Sheets
Specification includes a Sequence Listing.

(56) References Cited

OTHER PUBLICATIONS

Beckers et al., "Paleogenetic study of ancient DNA suggestive of X-linked acrogigantism." *Endocrine-Related Cancer* 24(2): L17-L20 (Epub Jan. 3, 2017).
Beckers et al., "X-linked acrogigantism syndrome: clinical profile and therapeutic responses," *Endocrine-Related Cancer* 22(3): 353-367 (Feb. 24, 2015).
Castinetti et al., "GPR101 mutations are not a frequent cause of congenital isolated growth hormone deficiency," *Hormone and Metabolic Research* 48(6): 389-393 (2016).
Cho-Clark et al., "GnRH-(1-5) transactivates EGFR in Ishikawa human endometrial cells via an orphan G protein-coupled receptor," *Molecular Endocrinology* 28(1): 80-98 (Nov. 21, 2013).
Daly et al., "GHRH excess and blockade in X-LAG syndrome," *Endocrine-Related Cancer* 23(3): 161-170 (Epub Dec. 15, 2015).
Daly et al., "Somatic mosaicism underlies X-linked acrogigantism syndrome in sporadic male subjects," *Endocrine-Related Cancer* 23(4): 221-233 (Epub Mar. 2, 2016).
Goldenberg et al., "Treatment of pituitary gigantism with the growth hormone receptor antagonist pegvisomant," *The Journal of Clinical Endocrinology & Metabolism* 93(8): 2953-2956 (Aug. 1, 2008).
Grossman et al., "The use of growth hormone-releasing hormone in the diagnosis and treatment of short stature," *Hormone Research in Paediatrics* 22(1-2): 52-57 (Jan. 1, 1985).
Hanson et al., "O24 molecular determinants for constitutive activity of GPR101, an orphan GPCR associated to X-linked acrogigantism syndrome (X-LAG)," *28th Conference of European Comparative Endocrinologists* (Aug. 2016).
Iacovazzo et al., "Germline or somatic GPR101 duplication leads to X-linked acrogigantism: a clinico-pathological and genetic study." *Acta Neuropathologica Communications* 4(56): 1-12 (Jun. 1, 2016).
International Search Report from the parent PCT Application No. PCT/US2015/060442, 7 pages (dated Feb. 25, 2016).
Naves et al., "Aggressive tumor growth and clinical evolution in a patient with X-linked acro-gigantism syndrome, " *Endocrine* 51(2): 236-244 (Epub Nov. 25, 2015).
Rostomyan et al., "Clinical and genetic characterization of pituitary gigantism: an international collaborative study in 208 patients," *Endocrine-Related Cancer* 22(5): 745-757 (Epub Jul. 17, 2015).
Trivellin et al., "Characterization of GPR101 transcript structure and expression patterns," *Journal Molecular Endocrinology* 57(2): 97-111 (Epub Jun. 9, 2016).
Trivellin et al., "Gigantism and acromegaly due to Xq26 microduplications and GPR101 mutation," *New England Journal of Medicine* 371(25): 2363-2374 (Dec. 18, 2014).
Trivellin et al., "Screening for GPR101 defects in pediatric pituitary corticotropinomas," *Endocrine-Related Cancer* 23(5): 357-365 (Epub Mar. 9, 2016).
Trivellin et al., "Stable GPR101 over-expressing cell lines as an invaluable tool for functional studies, ligand screening, and the identification of deregulated genes/pathways in patients with X-linked acrogigantism," Poster 269, *ENDO* 2017, 2 pages, (Apr. 1-4, 2017; downloaded from https://endo.confex.com/endo/2017endo/meetingapp.cgi/Paper/30998, Presented in Orlando, FL on Apr. 2, 2017).
Van Der Lely et al., "Long-term treatment of acromegaly with pegvisomant, a growth hormone receptor antagonist," *The Lancet* 358(9295): 1754-1759 (Nov. 24, 2001).
Written Opinion from the parent PCT Application No. PCT/US2015/060442, 9 pages (dated Feb. 25, 2016).

* cited by examiner

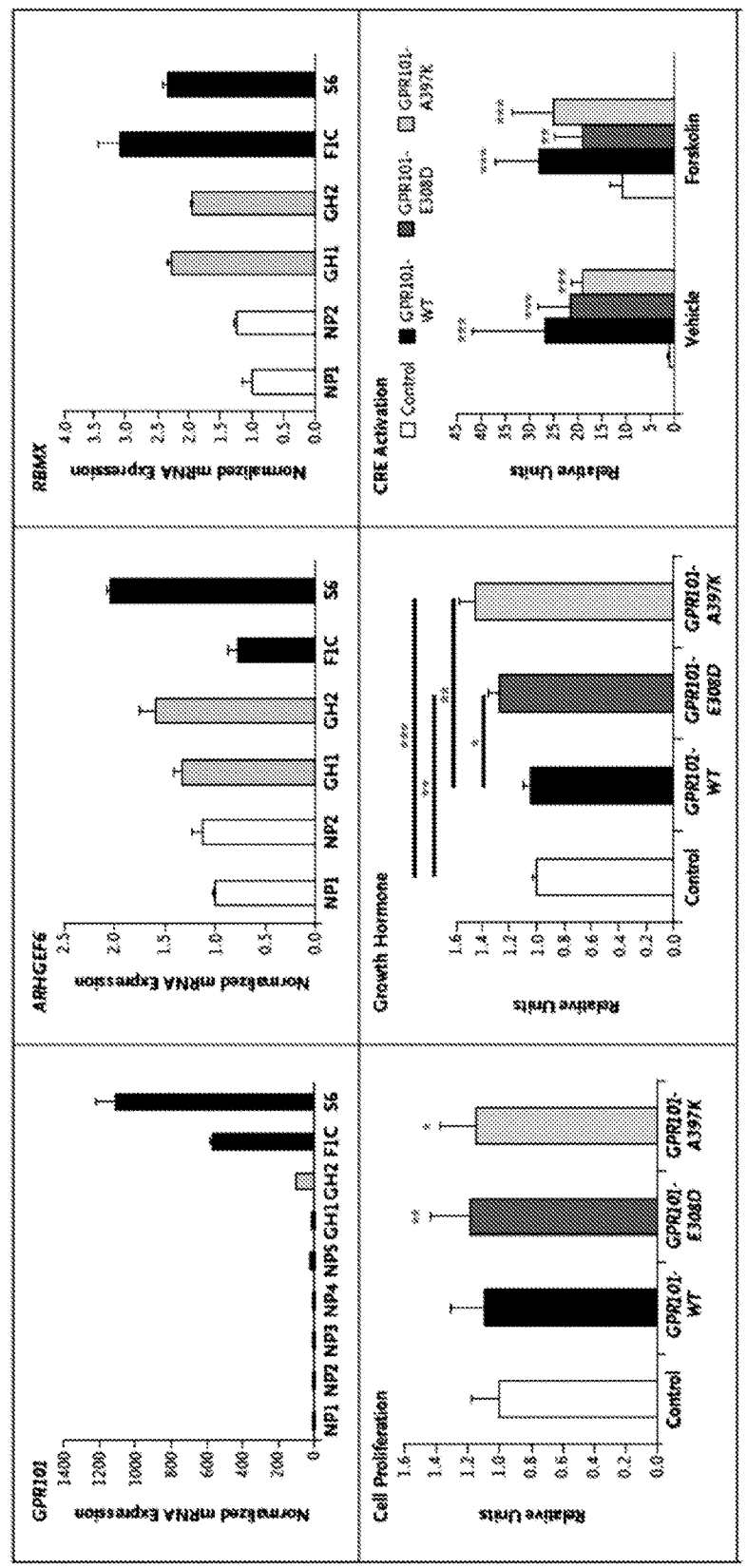

SEQUENCE LISTING

<160> NUMBER OF SEQ ID NOS: 6

<210> SEQ ID NO 1
<211> LENGTH: 1527
<212> TYPE: DNA
<213> ORGANISM: Homo sapiens

<400> SEQUENCE: 1

```
atgacgtcca cctgcaccaa cagcacgcgc gagagtaaca gcagccacac gtgcatgccc      60
ctctccaaaa tgcccatcag cctggcccac ggcatcatcc gctcaaccgt gctggttatc     120
ttcctcgccg cctctttcgt cggcaacata gtgctggcgc tagtgttgca gcgcaagccg     180
cagctgctgc aggtgaccaa ccgttttatc tttaacctcc tcgtcaccga cctgctgcag     240
atttcgctcg tggccccctg ggtggtggcc acctctgtgc ctctcttctg gccctcaac      300 agccacttct gcacggccct ggttagcctc acccacctgt tcgccttcgc cagcgtcaac     360
accattgtcg tggtgtcagt ggatcgctac ttgtccatca tccaccctct ctcctacccg     420
```

```
tccaagatga cccagcgccg cggttacctg ctcctctatg gcacctggat tgtggccatc    480
ctgcagagca ctcctccact ctacggctgg ggccaggctg cctttgatga gcgcaatgct    540
ctctgctcca tgatctgggg ggccagcccc agctacacta ttctcagcgt ggtgtccttc    600
atcgtcattc cactgattgt catgattgcc tgctactccg tggtgttctg tgcagcccgg    660
aggcagcatg ctctgctgta caatgtcaag agacacagct tggaagtgcg agtcaaggac    720
tgtgtggaga tgaggatga agagggagca gagaagaagg aggagttcca ggatgagagt    780
gagtttcgcc gccagcatga aggtgaggtc aaggccaagg agggcagaat ggaagccaag    840
gacggcagcc tgaaggccaa ggaaggaagc acggggacca gtgagagtag tgtagaggcc    900
aggggcagcg aggaggtcag agagagcagc acggtggcca gcgacggcag catggagggt    960
aaggaaggca gcaccaaagt tgaggagaac agcatgaagg cagacaaggg tcgcacagag   1020
gtcaaccagt gcagcattga cttgggtgaa gatgacatgg agtttggtga agacgacatc   1080
aatttcagtg aggatgacgt cgaggcagtg aacatcccgg agagcctccc acccagtcgt   1140
cgtaacagca acagcaaccc tcctctgccc aggtgctacc agtgcaaagc tgctaaagtg   1200
atcttcatca tcattttctc ctatgtgcta tccctggggc cctactgctt tttagcagtc   1260
ctggccgtgt gggtggatgt cgaaacccag gtaccccagt gggtgatcac cataatcatc   1320
tggcttttct cctgcagtg ctgcatccac ccctatgtct atggctacat gcacaagacc   1380
attaagaagg aaatccagga catgctgaag aagttcttct gcaaggaaaa gcccccgaaa   1440
gaagatagcc acccagacct gcccggaaca gagggtggga ctgaaggcaa gattgtccct   1500
tcctacgatt ctgctacttt tccttga                                        1527
```

<210> SEQ ID NO 2
<211> LENGTH: 508
<212> TYPE: PRT
<213> ORGANISM: Homo sapiens

<400> SEQUENCE: 2

```
Met Thr Ser Thr Cys Thr Asn Ser Thr Arg Glu Ser Asn Ser Ser His
  1               5                  10                  15

Thr Cys Met Pro Leu Ser Lys Met Pro Ile Ser Leu Ala His Gly Ile
             20                  25                  30

Ile Arg Ser Thr Val Leu Val Ile Phe Leu Ala Ala Ser Phe Val Gly
         35                  40                  45

Asn Ile Val Leu Ala Leu Val Leu Gln Arg Lys Pro Gln Leu Leu Gln
     50                  55                  60

Val Thr Asn Arg Phe Ile Phe Asn Leu Leu Val Thr Asp Leu Leu Gln
 65                  70                  75                  80

Ile Ser Leu Val Ala Pro Trp Val Val Ala Thr Ser Val Pro Leu Phe
                 85                  90                  95

Trp Pro Leu Asn Ser His Phe Cys Thr Ala Leu Val Ser Leu Thr His
            100                 105                 110

Leu Phe Ala Phe Ala Ser Val Asn Thr Ile Val Val Ser Val Asp
        115                 120                 125

Arg Tyr Leu Ser Ile Ile His Pro Leu Ser Tyr Pro Ser Lys Met Thr
    130                 135                 140

Gln Arg Arg Gly Tyr Leu Leu Leu Tyr Gly Thr Trp Ile Val Ala Ile
145                 150                 155                 160

Leu Gln Ser Thr Pro Pro Leu Tyr Gly Trp Gly Gln Ala Ala Phe Asp
                165                 170                 175
```

Glu Arg Asn Ala Leu Cys Ser Met Ile Trp Gly Ala Ser Pro Ser Tyr
            180                 185                 190

Thr Ile Leu Ser Val Val Ser Phe Ile Val Ile Pro Leu Ile Val Met
        195                 200                 205

Ile Ala Cys Tyr Ser Val Val Phe Cys Ala Ala Arg Arg Gln His Ala
    210                 215                 220

Leu Leu Tyr Asn Val Lys Arg His Ser Leu Glu Val Arg Val Lys Asp
225                 230                 235                 240

Cys Val Glu Asn Glu Asp Glu Glu Gly Ala Glu Lys Lys Glu Glu Phe
                245                 250                 255

Gln Asp Glu Ser Glu Phe Arg Arg Gln His Glu Gly Glu Val Lys Ala
            260                 265                 270

Lys Glu Gly Arg Met Glu Ala Lys Asp Gly Ser Leu Lys Ala Lys Glu
        275                 280                 285

Gly Ser Thr Gly Thr Ser Glu Ser Ser Val Glu Ala Arg Gly Ser Glu
    290                 295                 300

Glu Val Arg Glu Ser Ser Thr Val Ala Ser Asp Gly Ser Met Glu Gly
305                 310                 315                 320

Lys Glu Gly Ser Thr Lys Val Glu Glu Asn Ser Met Lys Ala Asp Lys
                325                 330                 335

Gly Arg Thr Glu Val Asn Gln Cys Ser Ile Asp Leu Gly Glu Asp Asp
            340                 345                 350

Met Glu Phe Gly Glu Asp Asp Ile Asn Phe Ser Glu Asp Asp Val Glu
        355                 360                 365

Ala Val Asn Ile Pro Glu Ser Leu Pro Pro Ser Arg Arg Asn Ser Asn
    370                 375                 380

Ser Asn Pro Pro Leu Pro Arg Cys Tyr Gln Cys Lys Ala Ala Lys Val
385                 390                 395                 400

Ile Phe Ile Ile Ile Phe Ser Tyr Val Leu Ser Leu Gly Pro Tyr Cys
                405                 410                 415

Phe Leu Ala Val Leu Ala Val Trp Val Asp Val Glu Thr Gln Val Pro
            420                 425                 430

Gln Trp Val Ile Thr Ile Ile Ile Trp Leu Phe Phe Leu Gln Cys Cys
        435                 440                 445

Ile His Pro Tyr Val Tyr Gly Tyr Met His Lys Thr Ile Lys Lys Glu
    450                 455                 460

Ile Gln Asp Met Leu Lys Lys Phe Phe Cys Lys Glu Lys Pro Pro Lys
465                 470                 475                 480

Glu Asp Ser His Pro Asp Leu Pro Gly Thr Glu Gly Gly Thr Glu Gly
                485                 490                 495

Lys Ile Val Pro Ser Tyr Asp Ser Ala Thr Phe Pro
            500                 505

<210> SEQ ID NO 3
<211> LENGTH: 29
<212> TYPE: PRT
<213> ORGANISM: Artificial Sequence
<220> FEATURE:
<223> OTHER INFORMATION: synthetic peptide

<400> SEQUENCE: 3

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

```
<210> SEQ ID NO 4
<211> LENGTH: 30
<212> TYPE: PRT
<213> ORGANISM: Artificial Sequence
<220> FEATURE:
<223> OTHER INFORMATION: synthetic peptide

<400> SEQUENCE: 4

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: synthetic peptide

<400> SEQUENCE: 5

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln
            20                  25                  30

<210> SEQ ID NO 6
<211> LENGTH: 44
<212> TYPE: PRT
<213> ORGANISM: Artificial Sequence
<220> FEATURE:
<223> OTHER INFORMATION: synthetic peptide

<400> SEQUENCE: 6

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
            35                  40
```

TREATMENT OF HORMONAL DISORDERS OF GROWTH

CROSS REFERENCE TO RELATED APPLICATIONS

This is a § 371 U.S. national stage of International Application No. PCT/US2015/060442, filed Nov. 12, 2015, which was published in English under PCT Article 21(2), which claims the benefit of U.S. Provisional Application No. 62/078,517, filed Nov. 12, 2014, which is incorporated herein by reference in its entirety.

FIELD

This relates to a method for treatment of hormonal disorders of growth and to the use of agents for treatment of hormonal disorders of growth, such as, but not limited to, acromegaly, gigantism, dwarfism, short stature, hypopituitarism and a disease of low levels of pituitary hormone secretion.

BACKGROUND

Secretion of hormones by glands of the endocrine system is responsible for regulating many important physiological processes in the body. The primary central regions that are responsible for controlling hormonal networks are the hypothalamus and the pituitary gland. Factors released by neurons in certain nuclei of the hypothalamus have stimulatory or inhibitory actions on the anterior pituitary gland cells. These anterior pituitary gland cells release hormones into the circulation, such as growth hormone (GH) and thyroid stimulating hormone, that, in turn, have potent effects on the production of growth factors and other hormones at the level of the liver, thyroid gland etc. Control of these systems is crucial to normal development across multiple animal species including humans. For instance, human GH secretion has a pattern that is pulsatile and diurnal: peaks of GH occur every two to four hours, usually at night. GH secretion is regulated by hormonal and biochemical factors. GH releasing hormone (GHRH) and somatostatin play opposite roles in modulating GH secretion: GHRH is a stimulator and somatostatin is an inhibitor. GHRH is released by neurons in the median eminence and the infudibular nucleus of the hypothalamus and this pulsatile release of GHRH is a potent stimulator of GH secretion from the anterior pituitary. GH stimulates IGF-I release from the liver and other tissues, which then feeds back to stimulate somatostatin and inhibit GHRH under normal circumstances.

Regulation of GHRH receptor (GHRH-R) and somatostatin receptor (SSTR) concentrations in the pituitary gland play an important role in the fine control of this system, as do the actions of other hormones such as estrogen and testosterone. However much remains to be learned about integration of systems of control at the hypothalamic level, where signals regarding body growth, energy utilization and sexual maturation need to be orchestrated so as to occur at the appropriate time. Other networks of hormone function controlled by the hypothalamus and pituitary, such as gonadotrope regulation of sexual development and fertility, corticotrope regulation of adrenal corticosteroid activity and thyrotrope regulation of thyroid hormone activity have similar processes of integrating peripheral feedback.

Dysfunction of the hypothalamus and the pituitary can, therefore, lead to profound disturbances in hormonal control of normal physiology. Underactivity of hypothalamic and pituitary hormone secretion leads to syndromes of hypopituitarism, which vary in severity depending on the variety of hormone axes affected. For example, deficiency in hypothalamic and pituitary signals governing GHRH and GH release caused by genetic mutations can lead to forms of short stature or dwarfism. Replacement therapy is required in these conditions depending on the deficient hormones; individuals with short stature or dwarfism due to GH deficiency in childhood can be treated with GH to increase final adult height.

When tumors occur in endocrine cells, this can lead to disruption of normal hormonal secretion, either by destruction of the gland by non-hormone secreting tumor cells and concomitant undersecretion of hormones, or by overgrowth of hormone secreting cells in the tumor, leading to hypersecretion of hormones. In the latter situation, the subject suffering from an endocrine tumor can suffer symptoms caused by growth of the tumor itself, combined with the effects of hormone over-secretion. In humans and other mammals, for example, a tumor of the pituitary gland may over-secrete active hormones GH or adrenocorticotropic hormone (ACTH), among others, leading to well-known diseases such as acromegaly-gigantism and Cushing disease, respectively. Endocrine gland tumors are associated with significant morbidity and increased mortality when not controlled by available therapies. For tumors of the pituitary gland, medical, surgical and radiotherapies are used, either alone or in combination, to control disease.

For example, GH hypersecretion by a pituitary tumor in a subject that has not finished pubertal growth (i.e. bone growth plates have not yet fused) can cause physical overgrowth, including increased height, leading to a disease called gigantism. In adults, similar GH secreting pituitary tumors cause a disease called acromegaly in which an overgrowth deformation of the face and extremities is accompanied by important morbidities of the metabolic system and cardiovascular system, among others. Diseases of the pituitary gland like acromegaly can be treated medically using a somatostatin analog, such as, octreotide or lanreotide. Neurosurgical resection of the tumor can be performed; either as a complete or partial resection (called "debulking"), and radiotherapy (conventional or targeted gamma-knife methods) is usually reserved for cases that do not respond to medical and surgical therapies. Somatostatin analogs are used in a number of settings for endocrine and neuroendocrine tumor control. They are used as a treatment for GH secreting tumors causing acromegaly and gigantism. When these therapies are ineffective, tumor growth and elevated hormone levels can lead to serious disease effects and can increase mortality. Other alternate therapies for acromegaly, gigantism and other disorders of pituitary hormone hypersecretion could be medically useful.

SUMMARY

In some embodiments, the use of a GPR101 inhibitor, antagonist or inverse agonist for preventive and/or therapeutic treatment of diseases selected from the group consisting of acromegaly and gigantism is disclosed.

In additional embodiments, the use of GPR101 agonist for use in preventive and/or therapeutic treatment of disorders selected from the group consisting of dwarfism, short stature, hypopituitarism and a disease of low levels of pituitary hormone secretion is disclosed.

In some embodiments, methods are disclosed for reducing hormone secretion from the hypothalamus and pituitary gland in a subject by administering a GPR101 antagonist.

In yet other embodiments, methods are disclosed for reducing hormone production by a pituitary tumor or hyperplasia in a subject by administering a GPR101 antagonist.

In additional embodiments methods are disclosed for reducing the growth velocity of a subject with a pituitary tumor or hyperplasia where said tumor or hyperplasia causes growth hormone over-secretion and increased height (the clinical disease of gigantism) by administering a GPR101 antagonist.

In other embodiments, methods are disclosed for reducing hormone production by a pituitary tumor or hyperplasia where said tumor or hyperplasia over-secretes growth hormone over-secretion and leads to the clinical disease of acromegaly by administering a GPR101 antagonist.

In some embodiments, methods are disclosed for reducing hormone production by a pituitary tumor or hyperplasia where the tumor or hyperplasia over-secretes prolactin (prolactinoma), causes Cushing's disease due to an adrenocorticotropic hormone (ACTH) secreting pituitary tumor, or a thyroid stimulating hormone (TSH) secreting pituitary adenoma, or pituitary tumors secreting a variety of different hormones by administering a GPR101 antagonist.

In additional embodiments, methods are disclosed for controlling the growth of a pituitary tumor where the tumor secretes functional hormone or no functional hormones (a non-functioning pituitary adenoma) by administering a GPR101 antagonist.

In further embodiments, methods are disclosed for increasing hormone production from the hypothalamus and pituitary gland in a subject by stimulating hormone production by administering a GPR101 agonist.

In yet other embodiments, methods are disclosed for increasing hormone production by the hypothalamus and pituitary in a subject where said subject has the disease of hypopituitarism and low levels of pituitary hormone secretion by stimulating hormone production by administering a GPR101 agonist.

In some embodiments, methods are disclosed for increasing hormone production by the hypothalamus and pituitary in a subject where said subject has the disease of dwarfism or short stature due to growth hormone deficiency by stimulating growth hormone production by administering a GPR101 agonist.

In additional embodiments, methods are disclosed for increasing the growth rate of a subject where said subject has the disease of dwarfism or short stature due to growth hormone deficiency by stimulating growth by administering a GPR101 agonist.

In further embodiments, disclosed is a GHRH inhibitor, antagonist or inverse agonist for use in the therapeutic treatment of X-linked acrogigantism (X-LAG syndrome).

In yet other embodiments, disclosed is a GH antagonist for use in the therapeutic treatment of X-linked acrogigantism (X-LAG syndrome).

In some embodiments, methods are disclosed for increasing body mass and/or body size of lifestock comprising administering to livestock an effective amount of a GPR101 agonist.

In addition, a non-human transgenic animal is disclosed, wherein cells in the transgenic animal express a transgene encoding GPR101 or overexpressing an endogenous GPR101 gene.

The foregoing and other features and advantages will become more apparent from the following detailed description of several embodiments, which proceeds with reference to the accompanying figures.

BRIEF DESCRIPTION OF THE DRAWINGS

FIGS. 1A-1F shows the results relating to the expression of GPR101 in Pituitary Tissue from Children with Xq26.3 Microduplications. The expression of GPR101 in pituitary tissue from children carrying Xq26.3 microduplications was increased by a factor as high as 1000, as compared with the expression in unaffected pituitary tissue (in five samples [NP1 through NP5] obtained on autopsy) and in pituitary tumors from two patients with sporadic acromegaly (GH1 and GH2) who tested negative for the microduplication (Panel A). These findings, which were obtained on quantitative reverse-transcriptase-polymerase-chain-reaction (qRT-PCR) assay and normalized by a housekeeping gene, contrast with those for two other genes, ARHGEF6 (Panel B) and RBMX (Panel C), in the duplicated stretch of DNA; neither of these two genes showed up-regulated expression. Also shown are cell proliferation (Panel D), growth hormone secretion (Panel E), and activation of DNA sequences called cyclic AMP response elements (CRE) (Panel F) in rat GH3 cells transfected with mutant (p.E308D and p.A397K) and nonmutant GPR101 constructs. Values for cells transfected with empty (control) vector were set at 1. Also shown are values for untreated cells (vehicle) and forskolin (which increases CRE activation). Data are expressed as the mean results of three to five independent experiments, each of which was performed in triplicate. The T bars indicate standard deviations. One asterisk denotes $P<0.05$, two asterisks $P<0.01$, and three asterisks $P<0.001$.

SEQUENCES

Figure 2B:
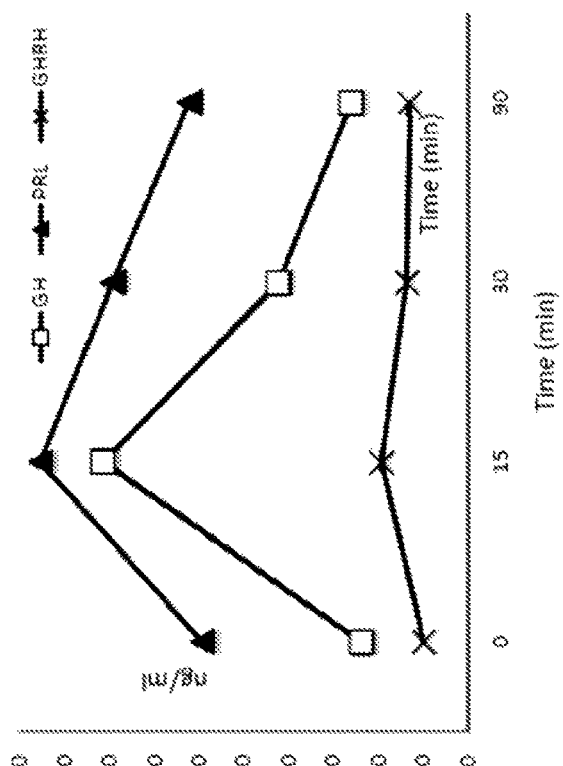
FIGS. 2A-2C show dynamic and pulsatility testing. Elevated growth hormone (GH), prolactin (PRL) and GHRH levels were seen throughout an extended testing period of 180 minutes (Panel A). GH levels are seen to peak at 150 min after an earlier GHRH rise between 105 min and 135 min. A TRH test induced an immediate and marked increase in GH levels and GHRH remained largely unchanged (Panel B). GnRH administration led to suppression of GH levels at 30 mins, whereas GHRH levels remained unaltered and prolactin rose mildly (Panel C).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file Sequence_Listing.txt, May 10, 2017, 8.46 KB, which is incorporated by reference herein.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Unless context indicates otherwise, a reference to "A or B" encompasses A, B, and both "A and B." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. Reference to the "invention" is descriptive of particular embodiments and is not meant to imply that any particular limitation is critical or essential for operation. In addition, the materials, methods, and examples are illustrative only and not intended to be limiting.

DETAILED DESCRIPTION

Methods are disclosed for treatment of hormonal disorders of growth and to the use of agents for treatment of hormonal disorders of growth, such as, but not limited to, acromegaly, gigantism, dwarfism, short stature, hypopituitarism and a disease of low levels of pituitary hormone secretion. Medicaments and therapies are disclosed for treatment of acromegaly, gigantism and other disorders of pituitary hormone hypersecretion.

When carrying out the studies for the present invention the present inventors have discovered a microduplication of a series of genes on chromosome Xq26.3 in human patients with gigantism due to GH and prolactin over-secreting pituitary adenomas occurring as children and in certain families with familial isolated pituitary adenomas. Among those genes, the only duplicated gene that was seen at increased levels in mRNA and immunohistochemical staining studies of pituitary tissues was GPR101. This increased expression of GPR101 and increased levels in tumor tissue was accompanied by an increase in numbers of GHRH receptors (GHRH-R), indicating that this gene duplication of GPR101 was having a direct effect on the pituitary tissue to increase the responsiveness to stimulatory signals from GHRH via activation of its receptor. Despite very high circulating GH and IGF-1 levels, the level of circulating GHRH was not inhibited as would be expected. Indeed the studies according to the present invention showed that in cases of microduplications involving GPR101 that increased circulating levels of GHRH are seen. In particular, it was subsequently demonstrated that such cases can have chronically elevated GHRH levels in the blood. Studies on the tumor of one such case demonstrated responsiveness in terms of GH and prolactin secretion to GHRH stimulation. This effect in the tumor could be blocked by a GHRH inhibitor. This further indicates an important dysregulation of pituitary growth-promoting signals due to the GPR101 duplication. The disease severity of these patients with duplicated GPR101 was also very remarkable, having pituitary tumors and hyperplasia at a very young age (<3 years), and the management of these cases was complicated by poor treatment responses. These data indicate that GPR101 duplication has a previously unrecognized role in the modulation of growth. Previous studies on GPR101 have not demonstrated that it plays a role in growth of the body or in increased secretion of GHRH, increased expression of GHRH-R or higher circulating levels of GH, IGF-1 and prolactin. Similarly this is the first data to note that GPR101 can play a role in the generation of pituitary tumors and can cause severe growth disorders.

Treatment of pituitary tumors such as those that cause gigantism and acromegaly is complex and multi-modal in many cases. Medical therapy with somatostatin analogs is associated with incomplete control in over 40% of cases. Other treatment options such as neurosurgery or radiotherapy are not suitable for all patients and can have significant side effects. Tumors of patients with gigantism due to pituitary tumors caused by microduplications involving the GPR101 gene can have increased GPR101 and GHRH-R levels in their tumors. Similarly these cases can have elevated circulating GHRH levels, indicating a hypothalamic disorder as this is the site of GHRH generation. GPR101 has been shown to be mainly present in regions of the hypothalamus and linked to the hypothalamus. Inhibition of GPR101 by an antagonist or downregulation of GPR101 by other means (e.g. small interfering RNA, anti GPR101 antibodies) can reduce tumor growth, decrease GHRH-R levels and normalize circulating GH, IGF-1 and prolactin levels. This has the effect of improving the health of the treated patient by decreasing the effects of over-secreted hormones on the patient.

In contrast, stimulation of GPR101 by an agonist or upregulation of GPR101 levels in patients with low endogenous pituitary hormone secretion (hypopituitarism) could increase circulating hormone production (e.g. GH) and reduce disease severity (e.g. increase vertical growth). This has the effect of improving the health of the treated patient by increasing the deficient hormone levels and reducing the effect of pituitary hormone deficiency on the patient.

In a first aspect, this invention relates to a method for reducing the effects of hormones secreted by tumors with increased levels of GPR101 in a human or a non-human subject, in whom this effect of reducing hormonal levels is to improve the health of the subject and such a method involves the administration of an antagonist or inverse agonist of GPR101.

In a first embodiment of said first aspect said subject is a mammal. It is preferable that said mammal is a human. It is more preferable that the subject is a human with a tumorous growth causing elevated levels of hormones in the blood that are deleterious to the health of the subject. More preferably still, the subject is a human with a tumor of the pituitary gland that secretes elevated levels of growth hormone causing gigantism or acromegaly. Again more preferably the subject with gigantism or acromnegaly is treated with an antagonist of GPR101 to reduce the secretion of growth hormone to levels compatible with normal health.

In a second aspect, the invention relates to a method for normalizing serum prolactin concentration in a human or non-human subject in whom such normalization is desirable. This method comprises administering to said subject an antagonist of GPR101.

In a first embodiment of this second aspect said subject is a mammal. Preferably said mammal is a human, more preferably a human whose blood plasma level of prolactin is higher than desired, and again more preferably still a human who is suffering from acromegaly or who is at risk of developing acromegaly or symptoms thereof. More preferably still the subject with elevated levels of prolactin is treated with an antagonist of GPR101 to reduce the secretion of prolactin to levels compatible with normal health.

In a third aspect, the invention relates to a method for normalizing serum insulin-like growth factor 1 (IGF-1) concentration in a human or non-human subject in whom such normalization is desirable. This method comprises administering to said subject an antagonist or inverse agonist of GPR101.

In a first embodiment of this third aspect said subject is a mammal. Preferably said mammal is a human, more preferably a human whose blood plasma level of IGF-1 is higher than desired, more preferably still a human who is suffering from gigantism or acromegaly. More preferably still the subject with elevated levels of IGF-1 is treated with an antagonist or inverse agonist of GPR101 to reduce the secretion of IGF-1 to levels compatible with normal health.

In a fourth aspect, the invention relates to a method for normalizing serum adrenocorticotropic hormone (ACTH) concentration in a human or non-human subject in whom such normalization is desirable. This method comprises administering to said subject an antagonist of GPR101.

In a first embodiment of this fourth aspect said subject is a mammal. Preferably said mammal is a human, more preferably a human whose blood plasma level of ACTH is higher than desired, more preferably still a human who is suffering from Cushing's disease. More preferably still the subject with elevated levels of ACTH is treated with an antagonist of GPR101 to reduce the secretion of ACTH to levels compatible with normal health.

In a fifth aspect, the invention relates to a method for normalizing serum cortisol concentration in a human or non-human subject in whom such normalization is desirable. This method comprises administering to said subject an antagonist of GPR101.

In a first embodiment of this fifth aspect said subject is a mammal. Preferably said mammal is a human, more preferably a human whose blood plasma level of cortisol is higher than desired, more preferably still a human who is suffering from Cushing's disease. More preferably still the subject with elevated levels of cortisol is treated with an antagonist or inverse agonist of GPR101 to reduce the secretion of cortisol to levels compatible with normal health.

In a sixth aspect, this invention relates to a method for increasing the secretion of hormones in a human or a non-human subject, in whom this effect of increasing hormonal levels is to improve the health of the subject and such a method involves the administration of an agonist of GPR101.

In a first embodiment of said sixth aspect said subject is a mammal. It is preferable that said mammal is a human. It is more preferable that the subject is a human with abnormally decreased levels of hormones in the blood that is deleterious to the health of said subject. More preferably still, the subject is a human with a deficiency of pituitary gland hormone secretion causing hypopituitarism. Again more preferably the subject is a human with a deficiency of pituitary gland hormone secretion that includes deficient growth hormone secretion leading to growth hormone deficiency and more preferably the subject is treated with an agonist of GPR101 to increase the secretion of growth hormone to levels compatible with normal health.

In a seventh aspect, this invention relates to a method for increasing the secretion of IGF-1 in a human or a non-human subject, in whom this effect of increasing hormonal levels is to improve the health of the subject and such a method involves the administration of an agonist of GPR101.

In a first embodiment of said seventh aspect said subject is a mammal. It is preferable that said mammal is a human. It is more preferable that the subject is a human with abnormally decreased levels of hormones in the blood that is deleterious to the health of said subject. More preferably still, the subject is a human with a deficiency of IGF-1 secretion leading to IGF-1 deficiency and more preferably the subject is treated with an agonist of GPR101 to increase the secretion of IGF-1 to levels compatible with normal health.

In a eighth aspect, this invention relates to a method for increasing the secretion of ACTH in a human or a non-human subject, in whom this effect of increasing hormonal levels is to improve the health of the subject and such a method involves the administration of an agonist of GPR101.

In a first embodiment of said eighth aspect said subject is a mammal. It is preferable that said mammal is a human. It is more preferable that the subject is a human with abnormally decreased levels of hormones in the blood that is deleterious to the health of said subject. More preferably still, the subject is a human with a deficiency of pituitary gland hormone secretion causing hypopituitarism. Again more preferably the subject is a human with a deficiency of ACTH secretion leading to ACTH deficiency and more preferably the subject is treated with an agonist of GPR101 to increase the secretion of ACTH to levels compatible with normal health.

In a ninth aspect, this invention relates to a method for increasing the secretion of cortisol in a human or a non-human subject, in whom this effect of increasing hormonal levels is to improve the health of the subject and such a method involves the administration of an agonist of GPR101.

In a first embodiment of said ninth aspect said subject is a mammal. It is preferable that said mammal is a human. It is more preferable that the subject is a human with abnormally decreased levels of hormones in the blood that is deleterious to the health of said subject. More preferably still, the subject is a human with a deficiency of cortisol secretion leading to cortisol deficiency and more preferably the subject is treated with an agonist of GPR101 to increase the secretion of cortisol to levels compatible with normal health.

Disclosed are the following, without limitation:

(1) A GPR101 inhibitor, antagonist or inverse agonist for use in preventive and/or therapeutic treatment of diseases selected from the group consisting of acromegaly and gigantism.

(2) The GPR101 inhibitor, antagonist or inverse agonist for use in preventive and/or therapeutic treatment according to (1), wherein said diseases are caused by a pituitary tumor or hyperplasia.

(3) The GPR101 inhibitor, antagonist or inverse agonist for use in preventive and/or therapeutic treatment according to (1) or (2), wherein said diseases are caused by over-secretion of growth hormone by a pituitary tumor or hyperplasia.

(4) The GPR101 inhibitor, antagonist or inverse agonist for use in preventive and/or therapeutic treatment according to (2) or (3), wherein said tumor or hyperplasia over-secretes prolactin (prolactinoma), causes Cushing's disease due to an adrenocorticotropic hormone (ACTH) secreting pituitary tumor, or a thyroid stimulating hormone (TSH) secreting pituitary adenoma, or pituitary tumors secreting a variety of different hormones.

(5) The GPR101 inhibitor, antagonist or inverse agonist for use in preventive and/or therapeutic treatment according to any one of (1) to (4), for use in controlling the growth of a pituitary tumor wherein the tumor secretes functional hormone or no functional hormones.

(6) The GPR101 inhibitor, antagonist or inverse agonist for use in preventive and/or therapeutic treatment according to (1), for reducing hormone secretion from the hypothalamus and pituitary gland.

(7) The GPR101 inhibitor, antagonist or inverse agonist for use in preventive and/or therapeutic treatment according to (1), for reducing hormone production by a pituitary tumor or hyperplasia.

(8) The GPR101 inhibitor, antagonist or inverse agonist for use in preventive and/or therapeutic treatment according to any one of (1) to (7), wherein the GPR101 inhibitor is selected from the group consisting of a monoclonal or polyclonal antibody specifically binding to GPR101, an antisense nucleic acid, small interfering RNA or chemical analogue of antisense nucleic acid or small interfering RNA specifically hybridizing to GPR101 mRNA or a chemical compound specifically inhibiting GPR101 activity, preferably the GPR101 inhibitor is a small interfering RNA or an anti-GPR101 antibody.

(9) The GPR101 inhibitor, antagonist or inverse agonist for use in preventive and/or therapeutic treatment according to any one of (1) to (8), wherein the GPR101 inhibitor is a small interfering RNA complementary to a target sequence comprised within the nucleic acid having the nucleotide sequence shown in SEQ ID NO: 1 or a fragment thereof.

(10) The GPR101 inhibitor, antagonist or inverse agonist for use in preventive and/or therapeutic treatment according to any one of (1) to (8), wherein the GPR101 inhibitor is an anti-GPR101 antibody specifically binding to GPR101 protein or to a protein consisting of or comprising the amino acid sequence shown in SEQ ID NO: 2 or a fragment thereof.

(11) A GPR101 agonist for use in preventive and/or therapeutic treatment of disorders selected from the group consisting of dwarfism, short stature, hypopituitarism and a disease of low levels of pituitary hormone secretion.

(12) The GPR101 agonist for use in preventive and/or therapeutic treatment according to (11), wherein the disease is due to growth hormone deficiency.

(13) The GPR101 agonist for use in preventive and/or therapeutic treatment according to (11) or (12), wherein the GPR101 agonist is GPR101 protein or a fragment thereof.

(14) The GPR101 agonist for use in preventive and/or therapeutic treatment according to (13), wherein the GPR101 agonist is GPR101 protein consisting of or comprising the amino acid sequence shown in SEQ ID NO: 2 or a fragment thereof.

(15) A method for reducing hormone secretion from the hypothalamus and pituitary gland in a subject by administering a GPR101 antagonist.

(16) A method for reducing hormone production by a pituitary tumor or hyperplasia in a subject by administering a GPR101 antagonist.

(17) A method for reducing the growth velocity of a subject with a pituitary tumor or hyperplasia where said tumor or hyperplasia causes growth hormone over-secretion and increased height (the clinical disease of gigantism) by administering a GPR101 antagonist.

(18) A method for reducing hormone production by a pituitary tumor or hyperplasia where said tumor or hyperplasia over-secretes growth hormone over-secretion and leads to the clinical disease of acromegaly by administering a GPR101 antagonist.

(19) A method for reducing hormone production by a pituitary tumor or hyperplasia where said tumor or hyperplasia over-secretes prolactin (prolactinoma), causes Cushing's disease due to an adrenocorticotropic hormone (ACTH) secreting pituitary tumor, or a thyroid stimulating hormone (TSH) secreting pituitary adenoma, or pituitary tumors secreting a variety of different hormones by administering a GPR101 antagonist.

(20) A method for controlling the growth of a pituitary tumor where the tumor secretes functional hormone or no functional hormones (a non-functioning pituitary adenoma) by administering a GPR101 antagonist.

(21) A method for increasing hormone production from the hypothalamus and pituitary gland in a subject by stimulating hormone production by administering a GPR101 agonist.

(22) A method for increasing hormone production by the hypothalamus and pituitary in a subject where said subject has the disease of hypopituitarism and low levels of pituitary hormone secretion by stimulating hormone production by administering a GPR101 agonist.

(23) A method for increasing hormone production by the hypothalamus and pituitary in a subject where said subject has the disease of dwarfism or short stature due to growth hormone deficiency by stimulating growth hormone production by administering a GPR101 agonist.

(24) A method for increasing the growth velocity of a subject where said subject has the disease of dwarfism or short stature due to growth hormone deficiency by stimulating growth by administering a GPR101 agonist.

(25) The method according to any one of (15) to (24), where the said subject is a human.

(26) The method according to any one of (15) to (24), where the said subject is a non-human animal.

(27) GHRH inhibitor, antagonist or inverse agonist for use in the therapeutic treatment of X-linked acrogigantism (X-LAG syndrome).

(28) GHRH inhibitor, antagonist or inverse agonist for use in the therapeutic treatment of X-linked acrogigantism according to (27), wherein the X-linked acrogigantism is characterized by gigantism occurring during infancy and a microduplication in chromosome Xq26.3 that includes the orphan G-protein coupled receptor (GPCR) gene, GPR101.

(29) GHRH inhibitor, antagonist or inverse agonist for use in the therapeutic treatment of X-linked acrogigantism according to (27) or (28), wherein the GHRH inhibitor, antagonist or inverse agonist is selected from the group consisting of pasireotide, octreotide, lanreotide, cabergoline and hGHRH peptide antagonist.

(30) GH antagonist for use in the therapeutic treatment of X-linked acrogigantism (X-LAG syndrome).

(31) GH antagonist for use in the therapeutic treatment of X-linked acrogigantism according to (30), wherein the X-linked acrogigantism is characterized by gigantism occurring during infancy and a microduplication in chromosome Xq26.3 that includes the orphan G-protein coupled receptor (GPCR) gene, GPR101.

(32) GH antagonist for use in the therapeutic treatment of X-linked acrogigantism according to (30) or (31), wherein the GH antagonist is pegvisomant.

(33) A method of increasing body mass and/or body size of lifestock comprising administering to livestock an effective amount of GPR101 agonist.

(34) The method of (33), wherein the livestock is selected from the group consisting of poultry, including chickens, goose, duck, turkey, pheasant, swine, cattle, sheep, and goat.

(35) A non-human transgenic animal, comprising as expressed transgene a gene encoding GPR101 or overexpressing endogenous GPR101 gene.

(36) The non-human transgenic animal according to (35), wherein the transgene comprises the nucleic acid sequence shown in SEQ ID NO: 1, or encodes a protein having the amino acid sequence shown in SEQ ID NO: 2.

(37) The non-human transgenic animal according to (35) or (36), being a non-human mammalian transgenic animal.

(38) The non-human transgenic animal according to (35) or (36), wherein the animal is selected from the taxononic groups of *Gallus* sp. (chicken), *Maleagris* sp. (turkey), Anatidae (duck, goose), Bovidae, in particular *Bos, Bubalus, Ovis; Sus* sp. (pig).

The present invention refers to medicaments and methods for treating growth disorders in a human or non-human subject. An inhibitor, antagonist or inverse agonist of GPR101, an orphan G-protein coupled receptor (GPCR), is used as medicament and is administrated to a subject for the purposes of reducing the secretion of hormones by the hypothalamus or pituitary gland or both. Said subjects will be individuals with tumors that have high levels of GPR101 expression due to an activating mutation of the GPR101 gene or a gene duplication or due to overexpression of the GPR101 protein. Preferred embodiments of the method include subjects with acromegaly or gigantism and high levels of GPR101 in pituitary or hypothalamic tissue, leading to stimulation of tumor growth and growth hormone and/or prolactin over-secretion by the pituitary gland in whom administration of a GPR101 inhibitor, antagonist or inverse agonist lowers hormone levels and reduces severity of acromegaly or gigantism.

The present invention also refers to GPR101 agonists for administration to individuals with inadequate secretion of hormones from the hypothalamus or pituitary gland or both. Said subjects will be individuals with low GPR101 activity due to an inactivating mutation of the GPR101 gene, or a deletion of the GPR101 gene or decreased expression of the GPR101 gene. Preferred embodiments include subjects with hypopituitarism leading to abnormally growth hormone secretion and short stature/dwarfism in whom administration of a GPR101 agonist leads to stimulation of hypothalamic and/or pituitary hormone secretion leading to increased circulating growth hormone and increased or normalized height.

The present invention also provides GHRH inhibitors, antagonists or inverse agonists and GH antagonists for use in the therapeutic treatment of X-linked acrogigantism (X-LAG syndrome). In particular, the X-LAG syndrome is characterized by gigantism occurring during infancy and a microduplication in chromosome Xq26.3 that includes the orphan G-protein coupled receptor (GPCR) gene, GPR101. Preferably, the GHRH inhibitor, antagonist or inverse agonist is selected from the group consisting of somatostatin analogs, in particular pasireotide, octreotide and lanreotide, dopamine agonists, in particular cabergoline, and hGHRH peptide antagonists. Further preferred, the GH antagonist is pegvisomant.

In addition, the present invention refers to a method of increasing body mass and/or body size of lifestock comprising administering to livestock an effective amount of GPR101 agonist. By stimulating the GPR101 activity using an GPR101 agonist it is expected that secretion of growth hormones increases which in turn leads to increased body mass and/or body size and consequently to a higher meat production by the livestock.

Further, the present invention is directed to a non-human transgenic animal, comprising as expressed transgene a gene encoding GPR101 or overexpressing endogenous GPR101 gene. Both approaches, i) expressing as transgene a gene encoding GPR101, ii) overexpressing endogenous GPR101 gene, will lead to an increase in growth hormone secretion and to increased body mass and/or body size, which in turn results in a higher meat production by the livestock.

Description of Several Embodiments

In particular, the present invention refers to agents for treatment of diseases selected from the group consisting of acromegaly and gigantism and to agents for treatment of diseases selected from the group consisting of dwarfism, short stature, hypopituitarism and a disease of low levels of pituitary hormone secretion. The present invention further provides a method of increasing body mass and/or body size of lifestock and a non-human transgenic animal.

The present invention relates to a method useful for the treatment of subjects with diseases of glands of the endocrine system that may lead to increased or decreased levels of hormones in the circulating blood. In particular this invention relates to the control of hormone secretion and tumor growth in subjects with increased levels of the orphan G Protein Coupled Receptor (GPCR), GPR101, in their pituitary and brain (e.g. hypothalamus) due to up-regulation or over-activity of the GPR101 gene. The invention relates also to stimulating hormone secretion in subjects with decreased levels of GPR101 in their pituitary and brain (e.g. hypothalamus) due to down-regulation or lack of function of the GPR101 gene. More particularly this invention relates to the inhibition of excessive pituitary hormone secretion and improvement in associated clinical symptoms (e.g. gigantism) from a pituitary tumor using a GPR101 inhibitor, antagonist or inverse agonist, or the stimulation of abnormally decreased pituitary hormone secretion and improvement in associated clinical symptoms (e.g. dwarfism) using a GPR101 agonist.

The present invention refers to a GPR101 inhibitor, antagonist or inverse agonist for use in preventive and/or therapeutic treatment of diseases selected from the group consisting of acromegaly and gigantism and to methods for preventive and/or therapeutic treatment of diseases selected from the group consisting of acromegaly and gigantism wherein to a subject GPR101 inhibitor, antagonist or inverse agonist is administered.

Further, the present invention provides a GPR101 agonist for use in preventive and/or therapeutic treatment of disorders selected from the group consisting of dwarfism, short stature, hypopituitarism and a disease of low levels of pituitary hormone secretion and to methods for preventive and/or therapeutic treatment of diseases selected from the group consisting of dwarfism, short stature, hypopituitarism and a disease of low levels of pituitary hormone secretion wherein to a subject GPR101 agonist is administered.

Moreover, the present invention provides GHRH inhibitors, antagonists or inverse agonists and GH antagonists for use in the therapeutic treatment of X-linked acrogigantism (X-LAG syndrome) and methods for therapeutic treatment of X-LAG syndrome, wherein to a subject GHRH inhibitor, antagonist or inverse agonist and/or GH antagonist is administered.

X-linked acrogigantism (X-LAG) syndrome is a form of inheritable pituitary gigantism that begins in early childhood and is usually associated with very elevated growth hormone (GH) and prolactin secretion by mixed pituitary adenomas. Microduplications on chromosome Xq26.3 that include the gene GPR101 underlie the genetic etiology of X-LAG syndrome.

Pituitary gigantism is a very recognizable but rare disorder. Patients with pituitary gigantism develop growth hormone (GH) excess from a pituitary tumor before closure of epiphyseal growth plates. The etiology of pediatric or adolescent pituitary tumors in general, and pituitary gigantism in particular, remains relatively obscure, with about 50% of cases of the latter having no known genetic cause. The most frequent known genetic cause is aryl hydrocarbon receptor interacting protein gene (AIP) mutations. During the studies according to the present invention a new condition, termed X-linked acrogigantism, (X-LAG) syndrome, was found. X-LAG syndrome is characterized by gigantism occurring during infancy. X-LAG syndrome patients develop pituitary adenomas/hyperplasia and greatly elevated growth hormone (GH) and insulin-like growth factor 1 (IGF-1) levels that are usually accompanied by hyperprolactinemia. Unlike other forms of pituitary gigantism due to single gene mutations/deletions, the underlying abnormality in X-LAG syndrome is a microduplication in chromosome Xq26.3 that includes the orphan G-protein coupled receptor (GPCR) gene, GPR101.

Patients with X-LAG syndrome usually develop pituitary macroadenomas, while a few have hyperplasia alone or in conjunction with adenoma. The elevated GH/IGF-1 levels are poorly responsive to somatostatin analogs despite the presence of ample somatostatin receptors. Control of growth and hormonal hypersecretion can be achieved by radical resection of the anterior pituitary. Residual tumor is capable of maintaining IGF-1 levels in the acromegalic range for many years, necessitating multimodal therapy. According to the present invention it was also found that the GH receptor antagonist pegvisomant represents a useful option for IGF-1 and growth control.

The terms GPR101, GPR101 protein and GPCR (orphan G Protein Coupled Receptor) as used herein are synonyms. GPR101 is highly expressed in hypothalamus and is predicted to couple to $G_s$, a potent activator of adenylyl cyclase. GPR101 protein is encoded by the gene GPR101. The amino acid sequence of GPR101 is shown in SEQ ID NO: 2. The nucleic acid sequence of the GPR101 mRNA is shown in SEQ ID NO: 1.

As used herein "inhibitor of GPR101" generally refers to an active agent, which selectively decreases or blocks the activity, the bioavailability and biological effects of GPR101. Preferably, the inhibitor of GPR101 is an active agent having one or more of the following activities: i) selectively decreasing or blocking binding of ligand to GPR101 protein, ii) selectively decreasing or blocking binding of a fragment of gonadotropin-releasing hormone, namely GnRH-(1-5), to GPR101 protein, iii) reducing or blocking cAMP pathway activation by GPR101, iv) downregulate GPR101 mRNA, protein and/or activity. Therefore, such inhibitor also may generally downregulate GPR101 mRNA, protein and/or activity, which includes reducing or blocking GPR101 mRNA transcription, translation, transport, GPR101 protein transport, folding, modification. As used herein the term "inhibitor" of GPR101 also comprises "antagonists" and "inverse agonists" of GPR101.

As used herein an antagonist of GPR101 is an active agent, which selectively decreases or blocks the activity, the bioavailability and biological effects of GPR101. Preferably, the antagonist of GPR101 is an active agent having one or more of the following activities: i) selectively decreasing or blocking binding of ligand to GPR101 protein, ii) selectively decreasing or blocking binding of a fragment of gonadotropin-releasing hormone, namely GnRH-(1-5), to GPR101 protein, iii) reducing or blocking cAMP pathway activation by GPR101.

The present invention also refers to inverse agonists of GPR101 Many GPCRs show spontaneous intrinsic constitutive activation when they are on the membrane surface. Therefore, if such GPCR is present it is "on" and do not require a ligand to activate the respective GPCR type. This GPCR type requires a different type of compound that would bind the receptor to switch it off, which then is termed an "inverse agonist".

Said inhibitor of GPR101 may be a monoclonal or polyclonal antibody specifically binding to GPR101, an antisense nucleic acid, small interfering RNA or chemical analogue of antisense nucleic acid or small interfering RNA specifically hybridizing to GPR101 mRNA or a chemical compound specifically inhibiting GPR101 activity. Preferably, the GPR101 inhibitor is small interfering RNA or anti-GPR101 antibody.

In another embodiment the GPR101 inhibitor is an antisense nucleic acid. Said antisense nucleic acid hybridises with GPR101 mRNA, which preferably has or comprises the nucleic acid sequence shown in SEQ ID NO: 1.

More preferred, the GPR101 inhibitor is an antisense nucleic acid or small interfering RNA complementary to a target sequence comprised within the nucleic acid having the nucleotide sequence shown in SEQ ID NO: 1 or a fragment thereof. Said small interfering RNA is used for silencing GPR101. Said antisense nucleic acid is for GPR101 knockdown. In a particularly preferred embodiment, the GPR101 inhibitor is an antisense nucleic acid molecule or small interfering RNA molecule that binds specifically to a complementary target sequence of GPR101 RNA. The GPR101 target sequence which is targeted by the siRNA is comprised within the nucleotide sequence shown in SEQ ID NO: 1. Silencing of GPR101 by small interfering RNA (siRNA) and GPR101 knockdown by antisense oligonucleotides has successfully been carried out in human endometrial cells by Cho-Clark et al. (*Mol. Endocrinol.*, 28 (1), 80-98 (2014).

In another preferred embodiment the GPR101 inhibitor is an anti-GPR101 antibody specifically binding to GPR101 protein or to a protein consisting of or comprising the amino acid sequence shown in SEQ ID NO: 2 or a fragment thereof.

Still further preferred, the GPR101 inhibitor is an anti-GPR101 antibody specifically binding to GPR101 protein or to a protein comprising one or more epitopes of GPR101 protein or one or more epitopes comprised within the amino acid sequence shown in SEQ ID NO: 2. Anti-GPR101 antibodies have already been described in the prior art (for example in U.S. Pat. No. 8,142,762 B2, Example 13: here rabbit polyclonal anti-GPR101 antibodies specific for the carboxy terminus of rat, mouse and human GPR101).

In one embodiment the GPR101 inhibitor is an antibody which may be a common antibody (which is composed of two heavy protein chains and two light chains), Fab fragments of a common antibody, single-chain variable fragments (scFV) or single-domain antibody (sdAb). Said antibody specifically binds to GPR101, which preferably has an amino acid sequence shown in SEQ ID NO: 2.

In yet another embodiment the GPR101 inhibitor is a fragment of GPR101, preferably a fragment of GPR101 which interferes with signaling. Said fragment of GPR101 is at least 8 consecutive amino acid residues and up to 10, 12, 15, 18, 20, 30, 50, 80, 100, 150, 200, 250, 300, 350, 400, 450, 500, consecutive amino acids in length of the amino acid sequence shown in SEQ ID NO: 2. The amino acid sequence of said fragment may have further deletions, additions and replacements of 1 to 20 amino acid residue positions.

The present invention also relates to GHRH inhibitors, antagonists or inverse agonists for use in the therapeutic treatment of X-linked acrogigantism (X-LAG syndrome). Preferably, the GHRH inhibitor, antagonist or inverse agonist is selected from the group consisting of somatostatin analogs, in particular pasireotide, octreotide and lanreotide, dopamine agonists, in particular cabergoline, and hGHRH peptide antagonists. Further preferred, the GH antagonist is pegvisomant.

Growth hormone releasing hormone (GHRH) is a peptide belonging to the secretin glucagon family of neuroendocrine and gastrointestinal hormones. Human GHRH (hGHRH) peptide is comprised of 44 amino acid residues. The best known site of production of GHRH is the hypothalamus. hGHRH is also produced by human malignant tissues (cancers) of diverse origin. Hypothalamic GHRH is an endocrine releasing hormone that, acting through specific GHRH receptors on the pituitary, which regulates the secretion of pituitary growth hormone (GH).

hGHRH peptide antagonists, also referred herein as "GHRH receptor antagonist", have been implicated in treating various disorders. GHRH peptide antagonists inhibit the proliferation of malignancies by indirect endocrine mechanisms based on the inhibition of pituitary GH release and resulting in the decrease of serum levels of GH and IGF-1, as well as by direct effects on the tumor tissue. Antagonistic analogs of GHRH can inhibit the stimulatory activity of GHRH and exert direct antiproliferative effects in vitro on cancer cells, and in vivo on tumors.

Various modifications of GHRH peptides confer antagonistic properties. The GHRH fragment comprising residues 1 to 29, or GHRH(1-29), is the minimum sequence necessary for biological activity on the pituitary. This fragment retains 50% or more of the potency of native GHRH. Many synthetic analogs of GHRH, based on the structure of hGHRH(1-29)NH$_2$ peptide have been prepared and were described in WO95/16707, WO97/42223, WO00/31336, U.S. Pat. Nos. 5,550,212, 5,942,489, 6,057,422, WO2014/004934 and US 2015/0166617, the disclosure of all of which is herein incorporated by reference in its entirety. The peptide hGHRH(1-29)NH$_2$ has the following amino acid sequence: Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$ (SEQ ID NO: 3). hGHRH(1-30)NH$_2$ has the following amino acid sequence: Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Ser-Ala-Arg-Gln- NH$_2$ (SEQ ID NO: 4). hGHRH(1-31)NH$_2$ has the following amino acid sequence: Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln- Asp-Ile-Met-Ser-Arg-Gln-Gln-NH$_2$ (SEQ ID NO: 5). Preferably, the hGHRH peptide antagonists comprises a GHRH peptide sequence to which amino acid deletions, insertions, and/or substitutions have been made. Further preferred, the hGHRH peptide antagonists is a fragment or modified fragment of hGHRH having the capability to bind to the hGHRH receptor and to inhibit or to reduce the release of growth hormone. These antagonistic properties are believed to result from replacement of various amino acids and acylation with aromatic or nonpolar acids at the N-terminus of hGHRH(1-29)NH$_2$, hGHRH(1-30)NH$_2$ and hGHRH(1-31)NH$_2$, respectively.

Therefore, particularly preferred hGHRH peptide antagonists for use in the therapeutic treatment of X-linked acrogigantism (X-LAG syndrome) are hGHRH peptide antagonists described in WO95/16707, WO97/42223, WO00/31336, U.S. Pat. Nos. 5,550,212, 5,942,489, 6,057,422 or WO2014/004934. In particular, the hGHRH peptide antagonist is a modified fragment of hGHRH, in particular hGHRH (1-29)NH$_2$, hGHRH(1-30)NH$_2$ or hGHRH(1-31)NH$_2$, wherein one or more amino acids are replaced and/or the N-terminus is acylated with aromatic or nonpolar carboxylic acids. More preferred, hGHRH peptide antagonists are selected from the group consisting of MIA-602, MIA-604, MIA-606, MIA-610, MIA-640 and MIA-690 described in WO2014/004934 WO2014/004934 and US 2015/0166617. The structure of MIA-602 is [(PhAc-Ada)$^0$-Tyr$^1$, D-Arg$^2$, Fpa$_5^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGHRH(1-29)NH$_2$, wherein PhAc is phenylacetyl, Ada is 12-aminododecanoyl, Fpa is mono- or poly-fluorinated Phe (fluorine substitutions on the aromatic ring), Fpa$_5$ is penta-fluorinated Phe (fluorine substitutions on the aromatic ring), Har is homoarginine, Me is methyl, Orn is ornithine, Abu is alpha-aminobutyric acid and Nle is norleucine. The remaining amino acid positions are as defined by the original sequence Tyr$^1$-Ala$^2$-Asp$^3$-Ala$^4$-Ile$^5$-Phe$^6$-Thr$^7$-Asn$^8$-Ser$^9$-Tyr$^{10}$-Arg$^{11}$-Lys$^{12}$-Val$^{13}$-Leu$^{14}$-Gly$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Met$^{27}$-Ser$^{28}$- Arg$^{29}$-NH$_2$ (SEQ ID NO: 3). It is noted that the amino acid residues from 30 through 44 of the native GHRH molecule do not appear to be essential to activity; nor does their identity appear to be critical. Therefore, it appears that the addition of some or all of these further amino acid residues to the C-terminus of the hGHRH(1-29)NH$_2$, hGHRH(1-30)NH$_2$ and hGHRH(1-31) NH$_2$ analogs will not affect the efficacy of these analogs as GHRH antagonists. If some or all of these amino acids were added to the C-terminus of the hGHRH(1-29)NH$_2$, hGHRH (1-30)NH$_2$ and hGHRH(1-31)NH$_2$ analogs, the added amino acid residues could be the same as residues 30 through 44 in the native hGHRH sequence (SEQ ID NO: 6) or reasonable equivalents.

The amino acid sequences of the synthetic peptides are numbered in correspondence with the amino acid residues in hGHRH(1-29) (SEQ ID NO: 3), hGHRH(1-30)NH$_2$ (SEQ ID NO: 4) and hGHRH(1-31)NH$_2$, (SEQ ID NO: 5), respectively. Thus, for example, the Ala$^4$ in the synthetic peptides occupy the same position in the sequence as the Ala$^4$ residue in hGHRH(1-29). The convention under which the N-terminal of a peptide is placed to the left, and the C-terminal to the right is also followed herein.

The present invention also relates to GH antagonists for use in the therapeutic treatment of X-linked acrogigantism (X-LAG syndrome). A preferred GH antagonist is pegvisomant. Pegvisomant (Somavert®) is a growth hormone receptor antagonist and is a pegylated and in terms of the amino acid sequence modified human growth hormone containing 191 amino acid residues. In the prior art pegvisomant is used in the treatment of acromegaly, in particular if the tumor of the pituitary gland causing the acromegaly cannot be controlled with surgery or radiation, and the use of somatostatin analogues is not successful. Pegvisomant blocks the action of growth hormone at the growth hormone receptor to reduce the production of IGF-1.

The present invention refers to a method of increasing body mass and/or body size of lifestock comprising administering to livestock an effective amount of GPR101 agonist. Administration of GPR101 agonist will increase GPR101 activity and hormone secretion. This will lead to increased body mass and/or body size and to a higher meat production by the livestock.

The term "livestock" refers to any livestock, or offspring of livestock, who is receiving treatment, is in need of treatment, is taking or receiving treatment for prevention purposes, and/or is being administered the composition.

The term "offspring" refers to progeny or descendants of livestock, and includes born progeny, fetuses and embryos. "Livestock" shall include poultry, including chickens, goose, duck, turkey, pheasant, swine, cattle, which includes beef and dairy production, sheep, and goat.

The term "administering" or "administration" includes any means for introducing the GPR101 agonist and other therapeutic agents, into the body, preferably into the systemic circulation. Examples include but are not limited to oral, including feed and/or drinking water, buccal, sublingual, pulmonary, ophthalmic, transdermal, transmucosal, as well as subcutaneous, intraperitoneal, intravenous, intramuscular injection, transplacental transfer and lactation. A "therapeutically effective amount" is an amount of an agent, such as a GPR101 agaoinist or antagonist, that is sufficient cause the desired effect, such as to treat a condition of interest.

The present invention is also directed to a non-human transgenic animal, comprising as expressed transgene a gene encoding GPR101 or overexpressing endogenous GPR101 gene. The GPR101 gene expressed as transgene in said non-human transgenic animal may be any animal, preferably mammalian GPR101 gene, for example human GPR101 gene. In an alternative approach the non-human transgenic animal is altered by genetic engineering, wherein the regulation of the expression of the respective endogenous GPR101 gene(s) is modified in that way that the endogenous gene is expressed at a higher rate compared to the wild-type or unmodified gene. Either of these modifications will lead to an increase in growth hormone secretion and to increased body mass and/or body size, resulting in a higher meat production by the livestock.

Somatic growth is orchestrated by a complex hormonal crosstalk involving the hypothalamus, pituitary, and peripheral tissues. Genetic disorders that affect this network can lead to increased secretion of growth hormone, which results in acromegaly. If the excess in growth hormone occurs before epiphyseal fusion, the result can be gigantism. Non-syndromic gigantism is most frequently caused by pituitary adenomas occurring as familial isolated pituitary adenomas or sporadically, usually as a result of mutations in the gene encoding aryl hydrocarbon receptor-interacting protein (AIP). Other monogenic diseases can cause gigantism, but most of these conditions develop in adulthood in association with other tumors. In young children, somatic overgrowth that is due to an excess of growth hormone is rare, and the cause is unknown. Other syndromic genetic overgrowth conditions in children, such as the Sotos syndrome and the Simpson-Golabi-Behmel syndrome, are not associated with pituitary abnormalities.

During the studies carried out for the present invention a striking phenotype of gigantism has been found that has an onset in early childhood and that is caused by an excess of growth hormone. The disorder is associated with heritable microduplications on chromosome Xq26.3. There are four genes in the duplicated stretch of DNA; one of these, GPR101, encodes an orphan G-protein-coupled receptor and is very likely the gene that drives the phenotype in young children and the growth of sporadic growth hormone-producing adenomas in some patients with acromegaly.

Several lines of evidence support the identification this new pituitary gigantism syndrome in young children carrying microduplications on chromosome Xq26.3. This disorder caused by GPR101 overexpression herein may be further referred to X-linked acrogigantism (X-LAG). First, no disruption of Xq26.3 was found in patients with later-onset gigantism. Second, the finding that patients with other conditions had different duplications within the same region narrowed the focus to the smallest region of overlap. A duplication encompassing CD40LG and ARHGEF6 but not RBMX and GPR101 occurred in a family with low birth weight, intellectual disability, and craniofacial abnormalities, which suggests that duplications with the exclusion of RBMX and GPR101 do not lead to gigantism. Third, short stature has been reported in several patients with deletions in this region, which suggests that the absence of these genes may lead to the opposite phenotype. Other investigators have described at least 15 additional patients with the same phenotype of early-onset growth who may be good candidates for a diagnosis of X-LAG.

The breakpoint features of Xq26.3 duplications suggest that they were generated by means of a replication-based mechanism that underlies the genesis of other copy-number variants (CNVs) and the pathogenesis of other genomic disorders.

The cytogenetic data narrowed the smallest region of overlap to a segment spanning CD40LG, ARHGEF6, RBMX, GPR101, one microRNA (miR-934), and a small nucleolar RNA (SNORD61) of unknown function. Expression of CD40LG in the pituitary tissues of the patients analyzed in these studies was not detected (FIG. 1). Messenger RNA for ARHGEF6 and RBMX was expressed to a similar degree in affected and unaffected tissues from duplication carriers. Of all the genes and the noncoding RNAs in the duplicated segment, only GPR101 had markedly increased expression in the pituitary tumors from the duplication carriers (FIG. 1). FIG. 1A shows that the expression of GPR101 in pituitary tissue from children carrying Xq26.3 microduplications was increased by a factor as high as 1000, as compared with the expression in unaffected pituitary tissue (NP1 through NP5) and in pituitary tumors from two patients with sporadic acromegaly (GH1 and GH2) who tested negative for the microduplication.

GPR101 is an orphan G-protein-coupled receptor that is strongly expressed in the hypothalamus in rodents. It was recently shown that a fragment of the gonadotropin-releasing hormone (namely GnRH-(1-5)) could be a ligand for this receptor. The effect of a mutation (p.A397K) that is predicted to activate GPR101 when tested in vitro and in mice supports such a role. The pituitary-specific overexpression of GPR101 may be due to a gene-dose effect (as described in many genomic disorders) or to an unknown promoter sequence created by the chromosomal rearrangement or to perturbed chromatin regulation due to the genomic structural alteration from duplication CNVs.

Unlike GPR101, neither ARHGEF6 nor RBMX was overexpressed in the pituitary tumors from children with microduplications.

The studies of sporadic acromegaly carried out for the present invention provide further support for a role of GPR101 in X-LAG. A recurrent GPR101 mutation was found, p.E308D, in 4.4% of DNA in tumor samples and in 1.9% of DNA in PBMC samples obtained from patients with isolated acromegaly. In at least one patient, the mutation was present only in the tumor DNA. GPR101 mutations in families with familial isolated pituitary adenomas were not identified. Transfection of a construct expressing GPR101 containing the p.E308D mutation increased proliferation and growth hormone secretion in a rat pituitary cell line. Moreover, it was shown that GPR101 can strongly activate the cAMP pathway, for which the mitogenic effects in pituitary somatotropes are well established. These data further support a role for variant GPR101 in sporadic acromegaly.

The mechanism by which mutant GPR101 contributes to increased growth hormone secretion is unclear. Some of the patients with early onset gigantism whom were evaluated in the studies of the present invention had normal or mildly elevated levels of circulating GHRH (but below the threshold required for ectopic tumoral secretion of this hormone). The tumor tissue showed strong expression of the growth hormone-releasing hormone receptor, in contrast to its expression of growth hormone-releasing hormone, which was low or absent.

In conclusion, the results of the studies of the present invention show that Xq26.3 microduplication is associated with a clinical syndrome of early-onset gigantism. An increased dose of GPR101 on chromosome Xq26.3 probably causes the disease, and its activation by mutation occurs in patients with sporadic acromegaly. Xq26.3 microduplications may explain other historical cases of gigantism with features that closely resemble those of X-LAG.

As mentioned above, during the studies for the present invention an Xq26.3 microduplication in the early-childhood form of gigantism was detected. Nine of the thirteen patients with the Xq26.3 microduplication and the one probable carrier (an affected mother with gigantism) were female and were of normal size at birth. They grew rapidly during infancy, attaining a median height score of +3.8 SD at diagnosis (median age: 36 months), at which point they showed marked overall somatic growth with elevated weight and enlarged head circumference (median: 51.2 cm). The onset of accelerated growth and the onset of accelerated weight gain usually coincided, but were not always synchronous. Compared with those who lacked the Xq26.3 microduplication, those with the microduplication had an earlier median age of abnormal growth onset (12 months vs. 16 years), increased height acceleration and elevated levels of IGF-1 and prolactin. Precocious puberty in the microduplication carriers was not detected. Levels of peripheral growth hormone releasing hormone (GHRH) did not suggest ectopic GHRH secretion, and nuclear imaging scans were negative. All patients who underwent surgery had pituitary macroadenomas alone (median maximum diameter: 16 mm), and three had pituitary hyperplasia with or without an identified adenoma. Hormonal control was not achieved with medical therapy alone; radical/repeated neurosurgery alone (n=4) or in combination with pegvisomant (n=3) or radiotherapy (n=2) was required. Seven patients had permanent hypopituitarism at the time of carrying out the studies for the present patent application.

The common duplicated genomic segment was approximately 500 Kb in length, from position 135,627,637 to 136,118,269 (GRCh37/hg19;). One patient had a complex genomic rearrangement, with two duplicated segments, and separated by a short region of normal genomic sequence. No other patterns of duplication/deletion or homozygosity were shared among affected cases. One FIPA family included an affected mother and two affected sons with the same Xq26.3 microduplication; the unaffected father did not have the duplication. In another FIPA family the mother had childhood-onset gigantism and a histologically-confirmed pituitary macroadenoma but had died of complications of hypopituitarism. She had two children: the son carried the Xq26.3 microduplication and had childhood-onset gigantism (patient F2A), and the healthy daughter did not have the duplication. The most parsimonious explanation is that the son inherited the X-linked disease from his carrier mother. Hence, the Xq26.3 microduplication can be considered a new pathogenic explanation in certain AIP mutation-negative FIPA acro-gigantism kindreds with familial isolated pituitary adenomas that have acrogigantism without AIP mutations.

Further Characterization of the Xq26.3 Microduplication

Using high-definition analysis of the critical duplicated region, 10 genomic duplications in the 13 genetically studied patients were analyzed, including four of the familial and eight sporadic cases. On aCGH these appeared to be simple duplications; however, high-resolution aCGH, long-range PCR and Sanger sequencing of the breakpoints revealed various underlying genomic complexities. All sporadic Xq26.3 duplications were non-recurrent; the boundaries of the duplicated segment where unique to each person. Both aCGH and assay by PCR yielded negative results for normal parents/siblings of sporadic cases. The same duplication was transmitted from F1A (affected mother) to her affected offspring, F1B and F1C. The two smallest regions of overlap (SRO), SRO1 and SRO2, were shared by the duplications: SRO1 (ChrX: 135627637-135986830, hg19) encompassed three OMIM genes, CD40LG (MIM#300386), ARHGEF6 (MIM#300267), and RBMX (MIM#300199), while SRO2 (ChrX: 136045310-136118269, hg19) included GPR101 (MIM#300393). (An SRO is the genomic region that is (in this study) duplicated and shared by all affected persons.)

Investigation of Candidate Genes

Sequencing each of the four genes in the 43 patients with gigantism did not reveal any single nucleotide variants of likely pathogenicity.

RT-qPCR of pituitary tumor RNA from two Xq26.3 microduplication patients suggested that CD40LG was not expressed in the pituitary tumors. Neither ARHGEF6 nor RBMX showed upregulated expression in the pituitary tumors of two patients with the duplication (FIG. 1). In contrast, the expression of GPR101 in the pituitaries of the children carrying a Xq26.3 duplication was up to 1000-fold higher than in unaffected pituitary tissue, and in pituitary tumors from persons who tested negative for the microduplication (FIG. 1A). This result was confirmed at the protein level by increased immunostaining for GPR101 in pituitary tumor from Xq26.3 duplicated cases. Experimental overexpression of ARHGEF6, RBMX, and GPR101 genes alone in the rat pituitary cell GH3 cell line did not significantly increase GH secretion or cell proliferation (FIGS. 1B and 1C); non-mutated GPR101 in combination with ARHGEF6 and/or RBMX modestly increased cell proliferation, but not GH secretion.

GPR101 as a Candidate Gene: Identification of the p.E308D Mutation

In a series of 248 patients with sporadic acromegaly, none carried a microduplication at Xq26.3. However, 11 of them carried a c.924G>C substitution (p.E308D) in GPR101, which was not found in 7600 controls from public databases. Of the 11 mutation carriers, three appeared to carry a constitutive mutation, which was detected in DNA from their PBMCs; the mutation was detected in the tumor DNA in the remaining eight cases. In one case, it was determined that the mutation was somatic (i.e., GPR101 sequence of DNA from PBMCs did not carry the mutation, whereas that of the tumor did. None of the 13 FIPA families with acromegaly carried the p.E308D GPR101 change.

GPR101 encodes an orphan GPCR that is highly expressed in rodent hypothalamus and is predicted to couple to $G_s$, a potent activator of adenylyl cyclase. Over-expression of the p.E308D and p.A397K mutants, but not non-mutated GPR101, significantly increased cell proliferation and GH secretion in rat GH3 cells (FIGS. 1D and 1E). Like the construct containing the non-mutant receptor, the two mutant constructs resulted in increased cAMP signaling in GH3 cells in an in vitro reporter assay, both at baseline and in the presence of forskolin (10 μM), a direct stimulator of adenylyl cyclase (FIG. 1F).

Clinical Observations and Results

A patient diagnosed to have X-LAG syndrome and elevated GHRH levels underwent surgery. In the studies for the present invention increased GHRH levels at all time points, ranging between 100-200 pg/ml, were found. These levels were seen against a backdrop of markedly elevated circulating GH and prolactin concentrations in excess of 200 ng/ml and 500 ng/ml at baseline. A pulsatility study showed elevations in GHRH, GH and prolactin throughout the 180 mins of the study. One peak of GHRH secretion was captured and was seemingly accompanied by a concomitant peak in GH but not prolactin secretion. The elevated GHRH was not markedly altered by TRH or GnRH administration. As no peripheral source of GHRH was found, these results indicate that GHRH hypersecretion is an intrinsic part of the etiology of X-LAG syndrome in some patients. Interestingly the pathology of pituitary disease in X-LAG syndrome bears strong resemblance to that seen in other cases of GHRH excess. It is known that central GHRH hypersecretion from hypothalamic gangliocytomas leads to pituitary adenoma and acromegaly. It was also known that hypersecretion of GHRH in mice transgenic for the human GHRH gene leads to the development of early and massive pituitary (somatotrope, mammotrope and somatomammotrope) hyperplasia. It was previously reported that in older transgenic mice, chronic GHRH hypersecretion leads to pituitary adenoma formation, predominantly with GH and prolactin staining. Further, it was known that peripheral GHRH hypersecretion from neuroendocrine tumors is accompanied by either pituitary somatotrope hyperplasia or mixed GH and prolactin secreting adenomas. Taken together, the sum effect of chronic GHRH hypersecretion on the pituitary is somatotrope, mammotrope and somatomammotrope hyperplasia and/or mixed GH and prolactin secreting adenomas. The fact that GHRH hypersecretion was found in combination with a similar pattern of pituitary histological changes suggests that X-LAG syndrome is a form of hypothalamic-onset pituitary tumorigenesis.

Further support for a role for GHRH hypersecretion in X-LAG syndrome comes from the in vitro pituitary culture data obtained during the studies for the present invention, which are the first results to be reported in a tumor from a known case of X-LAG syndrome. These results confirm basal GH and prolactin hypersecretion, which was further stimulated by GHRH co-incubation. Crucially, the addition of the GHRH antagonist acetyl-(D-Arg$^2$)-GHRH(1-29) was able to reduce basal and stimulated GH and prolactin secretion in a dose dependent manner. Co-incubation of acetyl-(D-Arg$^2$)-GHRH(1-29) with GHRH abolished the stimulatory effect of GHRH itself. This combination of findings suggests that clinical benefit could be yielded from pharmacological treatment with GHRH antagonists in X-LAG syndrome.

During the studies for the present invention a number of other stimulatory and inhibitory factors were investigated. Use of somatostatin analogs (SSA) such as octreotide did not lead to hormonal or growth control in X-LAG patients. These poor clinical responses to somatostatin receptor 2 (SSTR2)-specific somatostatin analogs in X-LAG syndrome were observed, despite strong immunohistochemical staining for SSTR2 in tumor samples. According to the studies, octreotide had no inhibitory effect on GH or prolactin in the X-LAG syndrome pituitary cell culture. Pasireotide had a small inhibitory effect on GH secretion, which suggests that some clinical benefit might be obtained in X-LAG syndrome via its binding at SSTR5 and SSTR3, as these receptor types are expressed in X-LAG syndrome tumor tissue (data not shown).

As some patients with X-LAG syndrome exhibit increased appetite in conjunction with their gigantism, the effects of ghrelin in the tumor tissue were studied. Ghrelin itself had a minor stimulatory effect on GH secretion, while a ghrelin receptor antagonist inhibited GH secretion at $10^{-8}$ and $10^{-7}$ M. These results suggest that patients with X-LAG syndrome may have GH dysregulation across various control pathways, although specific studies are needed.

According to further studies it was observed that in X-LAG patients postoperative use of pegvisomant resulted in control of IGF1 in all five X-LAG patients, where it was employed. Addition of pegvisomant permitted control of IGF1 and excessive growth in three patients who had previously undergone surgery and who also had developed multiple pituitary axis deficiencies. Among the nine patients who underwent primary surgical resection, three had immediate GH/PRL control and excessive growth was halted. For those patients in whom growth and GH secretion were not controlled by their initial surgery, the subsequent management was complex. Use of somatostatin analogs (SSA) (octreotide, lanreotide) and dopamine postoperatively did not lead to hormonal or growth control, which was only achieved with combinations of radiotherapy, repeated surgery, SSA, and finally pegvisomant. Therefore, it can be concluded that the GH receptor antagonist pegvisomant represents a useful option for IGF-1 and growth control.

In conclusion, the studies according to the present invention provide new evidence that GHRH dysregulation plays a role in the pituitary pathology and gigantism seen in X-LAG syndrome. Chronic GHRH hypersecretion in X-LAG syndrome leads to pituitary pathology that is similar to that seen in other experimental and clinical settings with GHRH excess. Inhibition of GH and prolactin secretion from tumor cell culture in X-LAG syndrome using a GHRH antagonist suggests that the challenging clinical management of X-LAG syndrome could be improved by targeting GHRH inhibition and GH receptor inhibition.

Treatment Protocols

The method for treatment of acromegaly and gigantism comprises administering to a patient an effective amount of the compound of the present invention.

Typically, the compounds of the present invention are administered in an amount of about 5 μg/kg per day to 3,000 μg/kg per day, and more preferably about 20 to 1,500 μg/kg per day preferably once or twice daily. However, other amounts, including substantially lower or higher amounts, may also be administered. The compounds of the invention are administered to a human subject in need of treatment by oral, intravenous, intraperitoneal, intramuscular, transdermal, nasal, iontophoretic, subcutaneous, intratumoral, administration or by any other acceptable route of administration.

Different amounts of the compounds of the present invention may also be administered as seen suitable by a practitioner for specific cases. For this or any other application the compounds of this invention may be administered in an amount of about 10 to 3,750 µg/kg, and more preferably about 15 to 1,600 µg/kg. Any means of administration is suitable. The foregoing ranges are, however, suggestive, as the number of variables in regard to an individual treatment regime is large, and considerable excursions from these recommended values are expected.

Formulations and Pharmaceutical Compositions

The following description refers to pharmaceutical compositions, which may contain the active agent of the present invention.

The compositions of the invention will be formulated for administration through ways known in the art and acceptable for administration to a mammalian subject, preferably a human. In some embodiments of the invention, the compositions of the invention can be administered by oral, intravenous, intraperitoneal, intramuscular, transdermal, nasal, iontophoretic, subcutaneous, intratumoral, administration or by any other acceptable route of administration. In further embodiments of the invention the compositions of the invention are administered "locoregionally", i.e., intravesically, intralesionally, and/or topically. In preferred embodiments of the invention, the compositions of the invention are administered systemically by injection, inhalation, suppository, transdermal delivery, etc. In further embodiments of the invention, the compositions are administered through catheters or other devices to allow access to a remote tissue of interest, such as an internal organ. The compositions of the invention can also be administered in depot type devices, implants, or encapsulated formulations to allow slow or sustained release of the compositions.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in *Goodman and Gilman's the Pharmacological Basis of Therapeutics,* 7th Edition (1985), MacMillan Publishing Company, New York, and *Remington's Pharmaceutical Sciences* 18*th Edition,* (1990) Mack Publishing Co, Easton Pa. Methods for administration are discussed therein, including oral, intravenous, intraperitoneal, intramuscular, transdermal, nasal, iontophoretic administration, and the like.

The compositions of the invention may be administered in a variety of unit dosage forms depending on the method of administration. For example, unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may be administered by use of solid compositions. For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more compositions of the invention, and more preferably at a concentration of 25%-75%.

For aerosol administration, the compositions of the invention are preferably supplied in finely divided form along with a surfactant and propellant. Typical percentages of compositions of the invention are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included, as desired, as with, e.g., lecithin for intranasal delivery.

The compositions of the invention can additionally be delivered in a depot-type system, an encapsulated form, or an implant by techniques well known in the art. Similarly, the compositions can be delivered via a pump to a tissue of interest.

The composition of the invention may also be provided in a kit as a slow-release composition such as a daily, weekly, monthly unit provided as a sponge, dermal patch, subcutaneous implant and the like in a wrapping or container. In this case, the patient may release a unit of the composition from the container and applies it as indicated in the kit instructions. The composition may then be replaced at the end of the specified period by a fresh unit, and so on.

The compound(s) of the present invention may be administered in a composition that also comprises one or more further drugs. The proportion of compounds of the present invention to the other drug(s) and carrier may be adjusted accordingly.

Antibodies

The present invention also refers to anti-GPR101 antibodies as GPR101 inhibitors directed to GPR101 protein which will partially or completely reduce the activity of this GPR101 protein. The present invention further provides compositions comprising antibodies that specifically bind to GPR101. In a preferred embodiment the protein GPR101 is having the amino acid sequence SEQ ID NO: 2. The antibodies may be monoclonal antibodies, polyclonal antibodies, antibody fragments or any combination thereof. In particular, said antibody may be a common antibody (which is composed of two heavy protein chains and two light chains), Fab fragments of a common antibody, single-chain variable fragments or single-domain antibody (sdAb). The antibodies may be formulated with a pharmaceutically acceptable carrier. In a preferred embodiment the antibodies specifically recognize and bind to GPR101 having the amino acid sequence SEQ ID NO: 2. Further preferred the antibodies specifically recognize an epitope (a stretch of 5 or more consecutive amino acid residues within the amino acid sequence shown in SEQ ID NO: 2).

The term "antibody," as used herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, including an antibody fragment. "Antibody" and "immunoglobulin" are used synonymously herein. An antibody fragment is a portion of an antibody such as F(ab')2, F(ab)2, Fab', Fab, Fv, scFv, Nanobodies and the like. Nanobodies (or single-domain antibodies (sdAb)) are antibody-derived therapeutic proteins that contain the unique structural and functional properties of naturally-occurring heavy-chain antibodies. The Nanobody technology was originally developed following the discovery that camelidae (camels and lamas) possess fully functional antibodies that lack light chains. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. The antibodies could be obtained using immunization in human and animals (mouse, rabbit, camel, lama, hen, goat).

Regardless of structure, an antibody fragment binds with the same antigen that is recognized by the full-length antibody, and, in the context of the present invention. Methods of making and screening antibody fragments are well-known in the art.

An anti-GPR101 antibody according to the present invention may be prepared by a number of different methods. For example, the antibodies may be obtained from subjects administered the recombinant polypeptide according to the present invention. In some embodiments, the antibodies may be made by recombinant methods. Techniques for making recombinant monoclonal antibodies are well-known in the art. Recombinant polyclonal antibodies can be produced by methods analogous to those described in U.S. Patent Application 2002/0009453, using the recombinant polypeptide according to the present invention as the immunogen(s). Said antibody obtained in accordance with the invention may be a murine, human or humanized antibody. A humanized antibody is a recombinant protein in which the CDRs of an antibody from one species; e.g., a rodent, rabbit, dog, goat, horse, camel, lama or chicken antibody (or any other suitable animal antibody), are transferred from the heavy and light variable chains of the rodent antibody into human heavy and light variable domains. The constant domains of the antibody molecule are derived from those of a human antibody. Methods for making humanized antibodies are well known in the art. More recently, it was reported that it is possible to generate hybridomas directly from human B-cells. Consequently, the recombinant polypeptide according to the present invention could be used to stimulate proliferation of human B-cell before to proceed to the generation of hybridomas.

The above-described antibodies can be obtained by conventional methods. For example, the recombinant polypeptide according to the present invention can be administered to a subject and the resulting IgGs can be purified from plasma harvested from the subject by standard methodology.

Antibody Compositions

The invention also refers to the preparation of antibodies and antibody compositions suitable for administration, such as compositions comprising an antibody and a pharmaceutically acceptable carrier. The antibody compositions may be formulated for any route of administration, including intravenous, intramuscular, subcutaneous and percutaneous, by methods that are known in the art. In one embodiment, the antibody composition provides a therapeutically effective amount of antibody, i.e., an amount sufficient to achieve a therapeutically beneficial effect.

In one embodiment, the antibody composition is an IVIG composition. As used herein, "IVIG" refers to an immunoglobulin composition suitable for intravenous administration. IVIG compositions may contain, in addition to immunoglobulin, a pharmaceutically acceptable carrier. The IVIG compositions may be "specific IVIG," meaning that the IVIG contains immunoglobulins that specifically bind to the antigen(s) represented by the recombinant polypeptide according to the present invention.

Treatment of Hormonal Disorders of Growth with Antibody Compositions

The present invention also refers to a method of treating hormonal disorders of growth by administering the above-described antibody compositions, such as the above-described IVIG compositions, to a subject in need thereof. A target patient population for the treatment of hormonal disorders of growth includes mammals, such as humans, who suffer from hormonal disorders of growth.

In accordance with one embodiment, the invention provides a method for treating hormonal disorders of growth using compositions comprising an antibody or antibodies directed to GPR101 according to the present invention, and a pharmaceutically acceptable carrier. In yet another embodiment, the antibodies are monoclonal antibodies.

A therapeutically effective amount of the antibody compositions can be determined by methods that are routine in the art. Skilled artisans will recognize that the amount may vary according to the particular antibodies within the composition, the concentration of antibodies in the composition, the frequency of administration, the severity of disease to be treated, and subject details, such as age, weight and immune condition. In some embodiments, the dosage will be at least 50 mg IVIG composition per kilogram of body weight (mg/kg), including at least 100 mg/kg, at least 150 mg/kg, at least 200 mg/kg, at least 250 mg/kg, at least 500 mg/kg, at least 750 mg/kg and at least 1000 mg/kg. Dosages for monoclonal antibody compositions typically may be lower, such as ⅒ of the dosage of an IVIG composition, such as at least about 5 mg/kg, at least about 10 mg/kg, at least about 15 mg/kg, at least about 20 mg/kg, or at least about 25 mg/kg. The route of administration may be any of those appropriate for a passive vaccine. Thus, intravenous, subcutaneous, intramuscular, intraperitoneal, intratumorally and other routes of administration are envisioned. As noted above, a therapeutically effective amount of antibody is an amount sufficient to achieve a therapeutically beneficial effect.

Antisense Oligonucleotides

The GPR101 inhibitor may be an antisense oligonucleotide, e.g. a small interfering RNA, being at least 8 nucleotides in length, preferably 8 to 1527, further preferred 8 to 500, still further preferred 8 to 200, even further preferred 8 to 80 nucleotides and particularly preferred 12 to 50, 13 to 40 and 15 to 30 nucleotides in length, which specifically hybridises with a nucleic acid molecule encoding GPR101, or which specifically hybridises to a nucleic acid having the nucleotide sequence shown in SEQ ID NO: 1, and is capable of inhibiting GPR101 expression.

In one embodiment the antisense oligonucleotide is 100% complementary to the nucleic acid molecule encoding GPR101.

The relationship between an antisense compound such as an oligonucleotide and its reverse complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent.

In the present invention, the targets are nucleic acids encoding GPR101; in other words, a gene encoding GPR101, or mRNA expressed from the GPR101 gene. mRNA which encodes GPR101 is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formyl-methionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding GPR101, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal role of the target molecule to cause a loss of function or activity, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include any vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The locations on the target nucleic acid to which the preferred antisense compounds hybridize are herein below referred to as "target segments." As used herein the term "target segment" is defined as at least an 8-nucleotide portion of a target region to which an active antisense compound is targeted. While not wishing to be bound by theory, it is presently believed that these target segments represent portions of the target nucleic acid which are accessible for hybridization.

While the specific sequences of certain target segments are set forth herein, one of skill in the art will recognize that these serve to illustrate and describe particular embodiments within the scope of the present invention. Additional target segments may be identified by one having ordinary skill.

Target segments 8-80 nucleotides in length comprising a stretch of at least eight consecutive nucleotides selected from within the illustrative preferred target segments are considered to be suitable for targeting as well.

Target segments can include DNA or RNA sequences that comprise at least the 8 consecutive nucleotides from the 5'-terminus of one of the illustrative target segments (the remaining nucleotides being a consecutive stretch of the same DNA or RNA beginning immediately upstream of the 5'-terminus of the target segment and continuing until the DNA or RNA contains about 8 to about 80 nucleotides). Similarly target segments are represented by DNA or RNA sequences that comprise at least the 8 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 8 to about 80 nucleotides). It is also understood that antisense target segments may be represented by DNA or RNA sequences that comprise at least 8 consecutive nucleotides from an internal portion of the sequence of an illustrative preferred target segment, and may extend in either or both directions until the oligonucleotide contains about 8 to about 80 nucleotides.

One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The overall effect of interference with mRNA function is decrease of the expression of GPR101. This decrease can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

As used herein the term "oligomeric compound" is defined as a polymeric compound substantially comprising nucleic acid based monomer subunits. Oligomeric compounds include oligonucleotides and their analogs, mimics or mimetics.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Certain preferred oligomeric compounds of the invention can have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage.

Oligonucleotide Mimetics

Another group of compounds of the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides. These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini.

In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

Antisense Compositions and Formulations

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Pharmaceutical Compositions and Routes of Administration

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer, intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

In some embodiments, an oligonucleotide may be administered to a subject via an oral route of administration. In some embodiments, non-parenteral (e.g. oral) oligonucleotide formulations according to the present invention result in enhanced bioavailability of the oligonucleotide. In this context, the term "bioavailability" refers to a measurement of that portion of an administered drug which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration.

Oligonucleotide compositions may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the oligonucleotides or mimetics thereof so administered.

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a an oligonucleotide and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

RNA Interference (RNAi) and siRNAs

RNA interference (RNAi) is a phenomenon that has developed into a new approach for elucidating and modulating gene function. RNAi is a sequence-specific, post-transcriptional, gene-silencing mechanism that is effected through RNA molecules, usually double stranded (dsRNA) that are homologous to a sequence of the target gene. Fragments of the dsRNA called "small interfering" RNAs (siRNAs) can rapidly induce loss of function, and only a few molecules are required in a cell to produce the effect through hybrid formation between a homologous siRNA and mRNA. A member of the RNase III family of nucleases named dicer has been identified as being involved in processing. DNA vector-mediated RNAi technology has made it possible to develop therapeutic applications for use in mammalian cells.

siRNA suppression or silencing of gene expression through a highly regulated enzyme-mediated process of RNAi involves multiple RNA-protein interactions characterized by four major steps: assembly of siRNA with the RNA-induced silencing complex (RISC), activation of the RISC, target recognition and target cleavage. These interactions may bias strand selection during siRNA-RISC assembly and activation, and contribute to the overall efficiency of RNAi.

Preferably, the inhibitory nucleic acid molecule is a double stranded nucleic acid, preferably an RNA, most preferably an siRNA used in a method of RNAi that results in sequence-specific silencing, e.g. via sequence-specific degradation of homologues in an mRNA. As used herein, the term siNA (small, or short, interfering nucleic acid) is meant to be equivalent to other terms used to describe nucleic acid molecules that are capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. Longer ds RNAi's, such a miRNAs, appear to tolerate mismatches more readily than do shorter dsRNAs. In addition, as used herein, the term RNAi is meant to be equivalent to other terms used to describe sequence specific RNA interference, such as post transcriptional gene silencing, or an epigenetic phenomenon. For example, siNA molecules of this are used to epigenetic ally silence genes at both the pre-transcriptional and, more commonly, the post-transcriptional level.

An siNA can be designed to target any region of the coding or non-coding sequence of an mRNA, preferably the coding sequence. The siRNA's exemplified herein are "targeted to" (which is synonymous with "specific for" or are "complementary to" or "hybridize with" or "hybridize to.")

coding sequences. A siNA or siRNA is preferably a double-stranded polynucleotide molecule comprising self-complementary sense and antisense regions, wherein the antisense region comprises a nucleotide sequence that is complementary to the nucleotide sequence in a target nucleic acid molecule or a portion thereof and the sense region has a nucleotide sequence corresponding to the target nucleic acid sequence or a portion thereof. The siNA can be assembled from two separate oligonucleotides, where one strand is the sense strand and the other is the antisense strand and wherein the antisense and sense strands are self-complementary. The siNA can also be assembled from a single oligonucleotide, where the self-complementary sense and antisense regions of the siNA are linked by means of a nucleic acid linker or a non-nucleic acid-based linker. The siNA can be a polynucleotide with a hairpin secondary structure, having self-complementary sense and antisense regions that create the hairpin. The siNA can be a circular single-stranded polynucleotide having two or more loop structures and a stem comprising self-complementary sense and antisense regions which circular polynucleotide can be processed either in vivo or in vitro to generate an active siNA molecule capable of mediating RNAi. The siNA can also comprise a single stranded oligo- or poly-nucleotide having nucleotide sequence complementary to a target nucleotide sequence in a target nucleic acid molecule or a portion thereof, wherein the single stranded oligo- or polynucleotide can further comprise a terminal phosphate group, such as a 5'-phosphate or 5',3'-diphosphate. In certain embodiments, the siNA molecule of the invention comprises separate sense and antisense sequences or regions, wherein the sense and antisense regions are covalently linked by nucleotide or non-nucleotide linkers as is known in the art, or are alternately non-covalently linked by ionic interactions, hydrogen bonding, Van der Waal's interactions, hydrophobic interactions, and/or stacking interactions.

As used herein, siNA molecules need not be limited to those molecules containing only RNA, but further encompasses chemically-modified nucleotides and non-nucleotides. In certain embodiments, the siNA molecules lack 2'-OH-containing nucleotides. In certain embodiments, siNA's do not require the presence of nucleotides having a 2'-OH group, and as such, siNA molecules may optionally not include any "ribonucleotides" (e.g., those nucleotides that have a 2'-OH group); these molecules can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. Such modified siNA molecules have also been referred to as short interfering modified oligonucleotides (siMON). Other chemical modifications, e.g., as described in WO 2003/070918 and WO2003074654 can be applied to any siNA sequence of the invention. In one embodiment, the molecule mediating RNAi has a 2 nucleotide 3' overhang. If the RNAi molecule is expressed in a cell from a construct, for example from a hairpin molecule or from an inverted repeat of the desired sequence, then the endogenous cellular machinery creates the overhangs.

Methods of making siRNAs are conventional. In vitro methods include processing the polyribonucleotide sequence in a cell-free system (e.g. digesting long dsRNAs with RNAse III or Dicer), transcribing recombinant double stranded DNA in vitro, and, preferably, chemical synthesis of nucleotide sequences homologous to GPR101 sequence.

Ribozymes and siNAs can take any of the forms, including modified versions, described for antisense nucleic acid molecules; and they can be delivered to cells and introduced into cells as oligonucleotides (single or double stranded) or in the form of an expression vector.

In a preferred embodiment, an antisense nucleic acid, siNA, preferably an siRNA comprises a single stranded polynucleotide comprising a sequence that is at least about 90% or at least about 91%, 92%, 93%, 94%, 95%, 96%, 97%, 98% or 99% identical to or complementary to a segment of the human GPR101 mRNA or coding DNA sequence (SEQ ID NO: 1). As used herein, a DNA and an RNA encoded by it are said to contain the same "sequence", taking into account that the thymine bases in DNA are replaced by uracil bases in RNA.

Active variants (e.g. length variants, including fragments; and sequence variants) of the nucleic acid-based inhibitors, preferably siRNAs, discussed herein are included. An "active" variant is one that retains the activity of the inhibitor from which it is derived (preferably the ability to inhibit GPR101 gene expression). It is routine to test a variant to determine its activity using conventional procedures.

As for length variants, an antisense nucleic acid or siRNA may be of any length that is effective for inhibition of the GPR101 gene/coding sequence. Typically, an antisense nucleic acid is from 6 to 50 nucleotides (e.g. at least 12, 15, 20, 25, 30, 35, 40, 45 or 50 nt), and may be as long as about 100 to about 200 nucleotides or more. Antisense nucleic acids may have the same length as the coding sequence to be inhibited. When referring to length, the terms "bases" and "base pairs" (bp) are used interchangeably, and will be understood to correspond to single stranded (ss) and double stranded (ds) nucleic acids.

The length of an effective siNA is generally from 15 bp to 29 bp, preferably from 19 to 29 bp, e.g. 15, 16, 17, 18, 19, 20, 21, 22, 23, 24, 25, 26, 27, 18 or 29 bp, with shorter and longer sequences being acceptable.

As for sequence variants, it is generally preferred that an inhibitory nucleic acid, whether an antisense nucleic acid, a ribozyme (the recognition sequences), a siNA, preferably a siRNA comprise a strand that is completely complementary to (or identical to the complement of) a sequence of the target sequence of a target nucleic acid that it is designed to inhibit. However, 100% complementarity/sequence identity is not required for the siRNA to function and thus be included within the scope of this invention. Thus, the siRNA of the present invention has the advantage of being able to tolerate and accommodate naturally occurring sequence variations, for example, in human GPR101 that might be expected due to genetic mutation, polymorphism, or evolutionary divergence and to encompass all known or yet unknown allelic variants thereof.

The degree of sequence identity may be optimized by sequence comparison and alignment algorithms well-known in the art. At least about 90% sequence identity is preferred (more preferably at least about 92%, 93%, 94%, 95%, 96%. 97%, 98% or 99%) between the inhibitory nucleic acid, preferably a siRNA, and the targeted nucleotide sequence of GPR101. Defined alternatively, an active variant of an inhibitory nucleic acid, preferably of a siRNA, of this invention is one that hybridizes to the sequence it is intended to inhibit under conditions of high stringency. For example, the duplex region of an siRNA may be defined functionally as a nucleotide sequence that is capable of hybridizing with a portion of the target gene transcript in vitro under high stringency conditions (e.g. 400 mM NaCl, 40 mM PIPES pH 6.4, 1 mM EDTA, 50° C. or 70° C., hybridization for 12-16 hours), followed generally by washing.

The disclosure is illustrated by the following non-limiting Examples.

EXAMPLES

Example 1: Array Comparative Genomic Hybridization (aCGH)

Samples were analyzed obtained from 43 patients with gigantism who had hypersecretion of growth hormone, evidence of an anterior pituitary lesion on magnetic resonance imaging, a height on country-specific growth charts of either more than the 97th percentile or more than 2 SD above the mean height for age, and negative test results for mutations or deletions in genes associated with pituitary adenomas. Genetic analyses delineated two phenotypes: an early-childhood form of gigantism with a typical onset in late infancy and a second form with a typical onset in adolescence.

In the gigantism population, all 43 patients underwent aCGH. DNA extracted from peripheral blood leukocytes underwent aCGH analysis using the following commercial arrays: 8×60K (G4827A-031746), and 4×180K (G4890A-029830) (Agilent Technologies, Santa Clara, Calif., USA) according to the manufacturer's instructions. The arrays were scanned with a G2565CA microarray scanner (Agilent Technologies, Santa Clara, Calif., USA) and the images were extracted and analyzed with CytoGenomics software v2.0 (Agilent Technologies, Santa Clara, Calif., USA). An ADM-2 algorithm (cut-off 6.0), followed by a filter to select regions with three or more adjacent probes and a minimum average log 2 ratio±0.25, was used to detect copy number changes. The quality of each experiment was assessed by the measurement of the derivative log ratio spread with CytoGenomics software v2.0. Genomic positions were based on the UCSC February 2009 human reference sequence (hg19) (NCBI build 37 reference sequence assembly). Filtering of copy number changes was carried out using the BENCHlab CNV software (Cartagenia, Leuven, Belgium).

In order to precisely determine the sizes, genomic boundaries and contents of the rearrangements in each individual, an 8×60K format aCGH (Agilent Technologies) was designed with high-density probes tiling the critical region inside Xq26.3 (ChrX: 135001882-136499429, hg19). The probe density averaged five oligonucleotides/Kb for the critical region with copy number changes. It also interrogates the flanking genomic regions of up to 2 Mb in size with probe density of 1-2 per Kb. The experimental procedures of aCGH, including DNA fragmentation, labeling and hybridization, are performed by following the protocols described previously with minor modifications.

Results

The critical region with genomic gains shared amongst the unrelated patients was previously identified by low-resolution whole-genome aCGH. Custom designed HD-aCGH interrogating the critical region delineated 10 different genomic duplications in 12 patients, including four familial and eight sporadic cases. The DNA of patient S3 was not of sufficient quality to be analyzed by HD-aCGH. The remaining 29 patients that did not shown any duplication in the Xq26.3 region by low-resolution whole-genome aCGH were also investigated in order to exclude an undetectable microduplication. HD-aCGH confirmed that these patients do not harbor any duplication in the studied region.

In the patients S1, S6, S7, S8, and S9, various sized microhomologies were observed at the breakpoint junctions, suggesting the FoSTeS/MMBIR (Fork Stalling and Template Switching/Microhomology-Mediated Break-Induced Replication) as the potential mechanism for the formation of this tandem duplications. Interestingly, one base-pair mismatch (C/G) was observed in the microhomology of S9, reflecting the possibility that a perfect match may not be always required for the microhomology to mediate FoSTeS/MMBIR mechanism. For case S5, a 5 bp insertion was observed. The FoSTeS/MMBIR may act as the mechanism for generating such complexity by switching the template twice. In the duplication of case S2, a 5 bp microhomology was observed at the breakpoint of the tandem duplication, while further sequencing revealed a 149 bp insertion that possibly arose from a copy of a template positioned on the reverse strand 122 Mb away (ChrX: 12865862-12866010, hg19). Flanking that 149 bp insertion were two 1 bp microhomologies (G and A). A similar level of complexity was apparent for the rearrangement in patient F2A. A 2 bp microhomology was observed at the breakpoint of the tandem duplication, with a 105 bp deletion and then a 1 bp insertion at the same place of the deletion. Non-homologous end-joining (NHEJ) or FoSTeS/MMBIR may act as the deletion/insertion mechanism.

More complex abnormalities were seen in the duplication of patient S4: HD-aCGH detected proximal and distal duplicated segments separated by a normal segment (this complexity was not seen on the whole genome low density array which simply showed a single duplicated region). Two major breakpoint junction clusters, S4-1 and S4-2, were revealed. A 3 bp insertion was observed at S4-1 and an insertion of 86 bp at the proximal S4-2, which could partially derive from mismatches in the vicinity (e.g. a 7 bp insertion and a 9 bp insertion). This 86 bp insertion also may provide the 7 bp microhomology for priming the replication to the distal end of S4-2.

PCRs of the breakpoint junctions specific for the patients were performed to confirm the inheritance pattern of the genomic gains. Breakpoint junction PCRs for the families of S2, S4 and S6 suggested the gains to be de novo events. The paternal sample was not available for S5. The breakpoint junction PCRs were negative in the mother and the unaffected brother. Breakpoint junction PCRs for the familial cases F1A, F1B and F1C revealed that the duplications in F1B and F1C were identical and inherited from the mother F1A. PCR was negative in the paternal DNA. For the other familial case F2A, the breakpoint junction PCR was negative for the unaffected sister of the proband.

In total, 21 potential template-switching events occurred in all the genomic gains, and microhomologies were involved in nine of them. Further, six small insertions (<10 bp) were observed, which may account for up to 12 template switches (2 template switches being required for each small insertion). Although the small insertions (less than 10 bp) were too small to be uniquely located in the genome, it is possible that there were microhomologies flanking the insertions, mimicking the mechanism of the insertion observed in S2. The small insertions could have also been de novo synthesized, rather than being template events. Five out of ten genomic gains showed multiple template switches, which introduced small-scale complexities near the large genomic gain breakpoints, reflecting the potential low-processivity replication repair and iterative template switches after the collapse of the replication forks.

Example 2: Copy Number Variation (CNV) Analysis

Individual CNV assays were performed by duplex TaqMan real-time PCR assays in order to confirm the array- CGH results in the giant patients and to extend the analysis in a cohort of 47 patients with sporadic pituitary tumors for which sufficient-quality DNA was available. CNV assays for CD40LG, ARHGEF6, RBMX, and GPR101, consisting in a pair of unlabeled primers and a FAM-labeled MGB probe, were supplied from Life Technologies (Assay ID: Hs02425845_cn, Hs01655699_cn, Hs01064297_cn, Hs01730605_cn, respectively). RNase P (Life Technologies, #4403328) with a VIC-labeled TAMRA probe was used as reference gene. TaqMan CMV assays were performed according to manufacturer's protocol (Life Technologies, Carlsbad, Calif., USA). Briefly, experiments were prepared in 96 microwell plates and consisted of 20 µl reactions containing 20 ng of genomic DNA, 10 µl TaqMan Genotyping Master Mix (Life Technologies, catalog number 4371355) and 1 µl each of one target gene and reference CNV assay mixes. All reactions were run in triplicate on a ViiA 7 Real-Time PCR System (Life Technologies) and thermal cycling conditions were 95° C., 10 min followed by 40 cycles of 95° C. for 15 s and 60° C. for 1 min. All data were analyzed using the CopyCaller software version 2.0 (Life Technologies). The copy number was determined by the relative relationship between the quantity of the target gene and the reference gene, using a female calibrator sample known to have two copies of each gene as the basis for comparison.

Results

Six patients harboring an Xq26.3 microduplications and 47 patients with sporadic acromegaly and pediatric pituitary tumors were analyzed for CNV by duplex TaqMan real-time PCR assays for CD40LG, ARHGEF6, RBMX, and GPR101. CNV assays confirmed the aCGH results in the patients with the duplication, whereas no gain or loss of genetic material was found in any gene in any sporadic acromegaly and pediatric patients. CNV analysis in the tumor DNA of two patients harboring the Xq26.3 duplication confirmed the duplication of all 4 genes in the pituitary tumor tissue.

Example 3: Whole Exome Analysis (WES)

Thirteen FIPA kindreds with homogeneous acromegaly (2-3 affected patients per kindred) were selected for WES and one affected individual per kindred was studied. Five patients from the gigantism population also underwent WES. Genomic DNA was extracted from 400 µl whole blood using the BioRobot M48 (Qiagen). Exome libraries were prepared from high quality DNA following vendors' protocols (TruSeq and Nextera exome capturing kits, Illumina with, respectively, 1 µg and 50 ng DNA). Exome libraries were multiplexed by 24 and paired-end sequenced on two lanes of an Illumina HiSeq reaching a mean 30× coverage depth. For each sample, reads were mapped and variants were called following the GATK Best Practices (GATK v3.1). Unless stated otherwise, steps were performed with GATK tools (v3.1). Briefly, paired-end reads were mapped to the reference human genome (UCSC hg19) with bwa-mem (0.7.7). Duplicate reads were marked with Picard (1.73) and locally realigned with MarkDuplicates. Base quality scores were recalibrated with BaseRecalibrator. Variants were called on each processed sample with the HaplotypeCaller in gVCF mode followed by a joint GenotypeGVCFs step including 1000 Genomes control samples. Variant quality scores were recalibrated with VariantRecalibrator and annotated with Variant Effect Predictor (Ensembl, release 75). Variants falling in a 99% truth sensitivity level were retained.

Example 4: Fluorescent In Situ Hybridization (FISH) Analysis

FISH analysis was performed for confirmation of the array data. Commercially available probes covering the region of chromosome X provided insufficient coverage and hence new fluorescent probes were designed in collaboration with the commercial partner (Agilent). The red and green probes were designed based on the continuous Xq26.3 duplication intervals of two of the sporadic cases, S1 and S2 (chrx:135620070-136173879, chrx:135617178-136250554) and the two separate duplicated intervals of case S4 (chrx: 135624323-135985727; chrx:136 045 379-136 268 105). This provided coverage of the two SROs identified in the Xq26.3 duplicated cases. The nuclei preparation was performed as described previously. Analysis was performed with a BX51 epifluorescence microscope (Olympus) equipped with a CV-M4+CL camera (JAI) and images were captured using the platform CYTOVISION version 7.3.1 (Leica Microsystems).

The specially designed fluorescent probes covering regions within SRO1 (green) and SRO2 (red) were applied to cultured leukocytes from four of the sporadic cases S1, S2, S4 and S9 (3 females and 1 male). In all four cases a duplication of the two probe signals was seen; a normal single copy of each probe signal was seen in the non-involved X chromosome of the 3 female cases.

Example 5: DNA Preparation and Sequencing Analysis

All patients with Xq26.3 microduplication, 37 pediatric sporadic patients from the NIH (32 ACTH-secreting and 5 GH-secreting adenomas without a history of FIPA or other inherited pituitary adenoma conditions), and 96 sporadic acromegaly patients (55% males; median age at diagnosis: 38.5 years) from the University of Liege (n=88) and the NIH (n=8) were sequenced for the four protein-coding genes (CD40LG, ARHGEF6, RBMX, and GPR101), the small nucleolar RNA, SNORD61, and the microRNA, miR-934, located in the duplicated Xq26.3 region. In addition, the GPR101 gene was sequenced in a large international cohort of sporadic acromegaly patients and somatic somatotropinoma samples from the NIH, European centers, and a group of samples of varied geographic origin. Among these sporadic acromegaly cases, 11 patients had paired genomic and somatic DNA available.

DNA was extracted from peripheral EDTA blood and pituitary tumor samples using the QIAamp DNA Mini Kit (Qiagen, Valencia, Calif.) according to the manufacturer's protocols. The whole coding region, intron-exon boundaries, and 5'- and 3'-UTRs of all five target genes were PCR amplified and directly sequenced. Primers sequences and PCR conditions are available upon request. DNA sequencing was performed using the BigDye 3.1 Termination Chemistry (Life Technologies) on a Genetic Sequencer ABI3100 apparatus (Life Technologies). Sequences were visualized and aligned to the corresponding wt reference sequence using the SeqMan Pro software (DNAStar, Madison, Wis.). All variants have been annotated according to Human Genome Variation Society (HGVS) recommendations (www.hgvs.org/mutnomen). The following reference sequences were used: NM_016267.3 for miR-934 (VGLL1), NM_000074.2 for CD40LG, NM_004840.2 for ARHGEF6, NM_002139.3 for RBMX, NR_002735.1 for SNORD61, and NM_054021.1 for GPR101.

Example 6: Immunostaining

The surgical samples were fixed in formalin and embedded in paraffin. Five-µm-thick sections were stained with haematoxylin-eosin (H&E) and reticulin for light microscopy. Immunohistochemistry for pituitary hormones was performed following previously described protocols using the following primary antibodies: anti-Prolactin (PRL) AM031-5M Biogenex®, Fremont, Calif., monoclonal mouse, ready to use; anti-Human Growth Hormone (GH) A0570 Dako Cytomation®, Carpinteria, Calif., polyclonal rabbit, working dilution 1:2000; anti-Adrenocorticotropin (ACTH) Clone 02A3 Dako Cytomation, Carpinteria, Calif., monoclonal mouse, working dilution 1:2000; anti-Follicle Stimulating Hormone (FSH), AM026-5M Biogenex, Fremont, Calif., monoclonal mouse, ready to use; anti-Luteinizing hormone (LH) AM030-5M Biogenex, Fremont, Calif., monoclonal mouse, ready to use; anti-Thyroid stimulating hormone (TSH) AM033-5M Biogenex, Fremont, Calif., monoclonal mouse, ready to use; anti-alpha-subunit (alpha-hCG) AM037-5M Biogenex, Fremont, Calif., monoclonal mouse, ready to use.

GHRH-R, ab150575, Abcam®, Cambridge, Mass., primary antibody is a rabbit polyclonal antibody mapping to the C-terminal transmembrane domain of GHRH-R. Immunohistochemistry was performed by Ventana® BenchMarkXT Automated IHC/ISH slide staining system. The histological samples were incubated for 90 min at 37° with this primary antibody diluted at 1:50, after pre-treatment with a pH9 buffer for 60 min. The Ventana® ultraView Universal DAB Detection Kit was used for the detection. GHRH, GTX81311, Genetex®, Irvine, Calif., primary antibody is a rabbit polyclonal antibody mapping to the N-terminal region of GHRH. Immunohistochemistry was performed by Ventana® BenchMarkXT Automated IHC/ISH slide staining system. The histological samples were incubated ×120' at 37° with this primary antibody diluted at 1:10, without pre-treatment. The Ventana® ultraView Universal DAB Detection Kit was used for detection. Cytokeratin staining was performed with CAM5.2. Normal pituitary, pancreatic, and gonadal tissues were used as positive controls.

Negative control reactions were obtained in each test series by omission of the primary antibody. Images from haematoxylin-eosin and reticulin stain for light microscopy and immunohistochemistry were performed with BX41 Olympus Microscope, Axiocam ICc 1 camera and Axiovision 4 software from Zeiss at 100× and 200× magnifications.

For GPR101 immunofluorescence evaluation, a subset of five human pituitary tumor tissues, a human normal pituitary tissue, and five human normal hypothalami, was used. All paraffin embedded slides were submitted to de-parafinization, rehydration and antigen retrieval for 30 min in citrate buffer solution (pH 6.0). All slides were incubated with 10% normal donkey serum (NDS) for one hour for blocking, and they were incubated with the following primary antibodies: rabbit anti-GPR101 (dilution 1:500; SAB4503289, Sigma-Aldrich, St. Louis, Mo., USA), rabbit anti-GPR101 (dilution 1:500; HPA001084, Sigma-Aldrich), goat anti-GH (dilution 1:100, sc-10364; Santa Cruz Biotechnology, Santa Cruz, Calif.) overnight at 4° C. Both anti-GPR101 antibodies react with the human and rodent homologues of GPR101. All slides were incubated for 1-2 hours with the following secondary antibodies: donkey anti-rabbit 555 (A-31572, Life Technologies, Foster City, Calif.) and donkey anti-goat 488 (A-11055, Life Technologies), both at 1:500 dilution. Prolong gold mounting media with DAPI (P36934, Life Technologies) was used to set the slides. As negative control, a section of the same specimen was incubated under identical conditions with no primary antibody. Fluorescence was analyzed with a Leica AF6000 microscope (Leica, Allendale, N.J.) at 63× magnification with fixed time of exposure for all samples. Subsequently, images were deconvoluted with the supplied Leica image processing software (Leica). The same linear adjustments for brightness, contrast and color balance have been applied with Adobe Photoshop CS6 to each entire image.

75,000 GH3 cells were seeded onto Lab-Tek II chamber slides (Nunc, Rochester, N.Y.), left overnight and transiently transfected with WT and mutant GPR101 vectors. 24 h after transfection cells were washed 2× in PBS and fixed in 4% paraformaldehyde in PBS for 15 min, followed by rehydration and permeabilization in PBS containing 0.01% Tween-20. Slides were blocked in 10% goat serum (Jackson ImmunoResearch, West Grove, Pa.) for 1 h. Two primary antibodies against GPR101 (SAB4503289, dilution 1:500, and HPA001084, dilution 1:1000, Sigma-Aldrich) in 10% goat serum were applied to the slides at 4° C. overnight alongside negative controls without primary antibody. Slides were washed in PBS-T and secondary Alexa Fluor 488 goat anti-rabbit (dilution 1:1000, Life Technologies) was applied for 1 h. Slides were washed, mounted using Prolong Gold containing DAPI (Life Technologies) and covered. Cells were visualized at 40× magnification with a Zeiss AxioCam MRm microscope camera using the ZEN software.

Five-µm-thick coronal sections of the mouse brain tissues were deparaffinized and the heat induced antigen retrieval was done in a microwave for 5 min with buffer containing 10 mM Tris, 1 mM EDTA, and 0.05% Tween 20, pH 9. The rabbit polyclonal anti-GPR101 antibody (SAB4503289, Sigma-Aldrich) was applied in 2 µg/ml dilution overnight at 4° C. Immunofluorescence staining was performed using a Tyramide signal amplification kit (T20922, Life Technologies) with horseradish peroxidase-goat anti-rabbit IgG and Alexa fluor 488 tyramide, according to the manufacturer's instructions. The sections were mounted in Mowiol and visualized under an inverted confocal microscope (Zeiss LSM 510). Brightness and contrast were adjusted in each entire image in Adobe Photoshop CS4.

Results

Immunostaining for GPR101 (red) and GH (green) was performed in five patients with the Xq26.3 microduplication and in controls (an age-matched control somatotropinoma without the duplication and a normal pituitary). A higher GPR101 expression was observed in patients harboring the Xq26.3 duplication compared to both controls.

Immunostaining for GPR101 was also performed in the mouse and human normal brain. GPR101 expression was observed in the mouse hypothalamic area around the third ventricle (3V), including the arcuate nucleus (ARH). In both the mouse and human ARH, GPR101 was detected on neuronal cell bodies and axons.

Haematoxylin-eosin (H&E) and reticulin staining were performed in all cases. In general, cases were of the mixed-type of GH and prolactin secreting adenoma (WHO 2004 Classification). Tumor cells showed eosinophilia and were organized in solid pattern with some cystic structures and psammomas. The tissue architecture was characterized by expended hyperplastic acini with intact reticulin fiber network compared to normal adenohypophysis. Some areas with enlarged, hyperplastic acini showed an initial breakdown of some reticulin fibers, resulting in confluent acini (transformation areas). Other zones presented clearly a partial or total disruption of reticulin fiber network with pseudo-nodular formations (microadenoma). In patient F1C the normal pituitary tissue was extensively substituted by mammosomatotroph hyperplasia with nodular pattern. There were small foci where the enlarged acini of the hyperplasia become confluent. GHRH-R was expressed in GH-secreting cells in normal adenohypophysis, but at low intensity. In contrast, GHRH-R immunostaining was positive in hyperplastic areas and in adenomas with intensity stronger than normal adenohypophysis. GHRH staining was performed and was low/absent in tumor or hyperplasia from patients with duplication, similar to that of normal pituitary tissue.

Example 7: RNA Isolation, Reverse Transcription and mRNA Expression Analysis

Total RNA was isolated from PHA stimulated blood cells using the RNeasy Mini Kit (Qiagen, Germantown, Md.). Prior to RNA extraction, in order to reduce nonsense-mediated mRNA decay, cells were incubated with 100 µg/ml cycloheximide (Sigma-Aldrich) for 2 h at 37° C. Total RNA was isolated from human and mouse pituitary tissues using TRIzol reagent (Life Technologies). 1 µg of RNA was treated with DNase I (Life Technologies) to remove genomic DNA contamination and then reverse transcribed to cDNA using the Superscript III Kit (Life Technologies) according to the manufacturer's protocols. Total RNA was isolated from GH3 cells transiently transfected with human WT and mutant GPR101 vectors (see below) using the RNeasy Mini Kit (Qiagen) according to the manufacturer's protocols, and reverse transcribed as described above. Total RNA from mouse hypothalamus and Poly A+ RNA from human hypothalamus were purchased from Clontech (catalog number 636664, 636144, respectively) and reverse transcribed as described above.

mRNA Expression Analysis

The expression levels of the four duplicated genes and GHRH were measured by RT-qPCR with the TaqMan system using ready-made probe-primer kits supplied from Life Technologies (Assay ID: CD40LG, Hs00163934_m1; ARHGEF6, Hs00374462_m1; RBMX, Hs00953944_g1; GPR101, Hs00369662_s1; GHRH, Hs00184139_m1). Reactions were performed in triplicate and GAPDH (glyceraldehyde-3-phosphate dehydrogenase, Life Technologies, Hs99999905_m1) was used as endogenous control. In GH3-transfected cells beta-actin (Actb) was used as endogenous control (Rn00667869_m1, Life Technologies). In mouse tissues Gpr101 expression was measured with TaqMan assay ID Mm01296083_m1 (Life Technologies) and normalized on beta-actin expression (Actb, Mm00607939_s1, Life Technologies). TaqMan assays were performed according to the manufacturer's protocol (Life Technologies). Briefly, experiments were prepared in 96 microwell plates and consisted of 20 µl reactions containing 20 ng of cDNA, 10 µl TaqMan Gene Expression Master Mix (Life Technologies, catalog number 4369016) and 1 µl each of one target gene and endogenous control assay mixes. All reactions were run on a ViiA 7 Real-Time PCR System (Life Technologies) and thermal cycling conditions were 95° C., 10 min followed by 40 cycles of 95° C. for 15 s and 60° C. for 1 min. Relative gene expression data were analyzed using a relative standard curve using qPCR human reference cDNA, random-primed (50 ng/µl, 639654, Clontech). Data analysis was performed using the ViiA 7 software (Life Technologies).

Results

The transcriptional levels of CD40LG, ARHGEF6, RBMX, and GPR101 were evaluated on peripheral RNA obtained from two patients with Xq26.3 micro duplications and compared with three normal subjects. CD40LG levels do not differ between patients and controls, whereas the mRNA levels of ARHGEF6, RBMX, and GPR101 are lower in peripheral RNA in the patients; this was particularly evident for GPR101. The transcriptional levels of GHRH were evaluated in two patients with the Xq26.3 duplication and compared with two normal pituitaries and two sporadic GH secreting adenomas. None of the analyzed samples showed expression of GHRH.

Example 8: Protein Extraction and Western Blot Analysis

Proteins were extracted from GH3 cells transiently transfected with WT and mutant GPR101 vectors. 24 h after transfection cells were washed with PBS, lysed with 100 µl of lysis buffer (50 mM Tris-HCl, 50 mM NaCl, 10 mM EGTA, 10 mM EDTA, 80 M sodium molybdate, 5 mM sodium pyrophosphate, 1 mM sodium orthovanadate, 1 mM PMSF, 4 mM pNPP, 1% Triton; Sigma-Aldrich), sonicated, and centrifuged at 20,000 g for 15 min at 4 C. The supernatant was subsequently measured for protein content using the BCA Protein Assay Kit (Pierce Biotechnology, Rockford, Ill.).

Proteins were also isolated from two post-mortem samples of normal human pituitary using 350 µl of lysis buffer (see above), sonicated, and centrifuged at 20,000 g for 15 min at 4 C. Pools of tissue-specific total proteins isolated from different human brain regions (amygdala, hippocampus, hypothalamus) were purchased from Clontech (catalog number 635317, 635319, 635320, respectively).

Under denaturing conditions, 15-30 µg of protein lysates were loaded onto Bolt 10% Bis-Tris Plus gels (Life Technologies) and electroblotted onto Whatman Protran nitrocellulose membranes (Sigma-Aldrich). Blots were blocked for 30 min in 5% non-fat dry milk in TBST 0.1% and incubated overnight with primary antibodies (GPR101 (SAB4503289, dilution 1:500, Sigma-Aldrich), and GAPDH (sc-137179, dilution 1:400, Santa Cruz)). Subsequently, blots were washed with TBST 0.1% (3×15 min) and incubated in goat anti-rabbit IgG horseradish peroxidase-conjugated secondary antibody (dilution 1:2000, Jackson ImmunoResearch) for 1 h at room temperature. Immunoblots were visualized using the Supersignal West Pico Chemiluminescent substrate (Thermo Scientific, Waltham, Mass.) on a ChemiDoc MP imaging system (Bio-Rad, Hercules, Calif.), and quantified using the Image Lab software (Bio-Rad). Expression was normalized to GAPDH.

Results

GPR101 protein expression in normal human pituitary, amygdala, hippocampus, and hypothalamus was analyzed by Western Blot. GPR101 expression was detected in all the three brain regions analyzed, whereas only one out of two normal pituitary samples showed low expression levels.

Example 9: Cell Culture, GH Secretion after ARHGEF6, RBMX, and GPR101 Over-Expression The rat pituitary somatomammotroph GH3 cell line was grown in Dulbecco's modified Eagle's medium (DMEM, high glucose, pyruvate, no glutamine; 10313, Life Technologies) supplemented with 10% fetal bovine serum (100-106, Gemini Bio-Products), and 1% antibiotic-antimycotic (15240-062, Life Technologies) in a humidified atmosphere at 37° C. with 5% $CO_2$.

GH3 cells were seeded in 12-well plates at a density of $2 \times 10^5$ cells/well. After 24 h, cells were starved with DMEM without serum for 16 h and then transfected with LIPO-FECTAMINE® 2000 (11668030, Life Technologies) according to the manufacturer's protocol, using OPTI-MEM® I Reduced Serum Medium (31985-070, Life Technologies) and 1 µg of each vector, alone or in combination. The human GPR101 wt (NM_054021.1) and ARHGEF6 wt (NM_004840) coding sequences cloned into the pCMV-XL5 vector were purchased from Origene (SC120214 and SC100230, respectively), while the human wt RBMX coding sequence (NM_002139) cloned into the pcDNA3.1N/V5-His TOPO vector (Life Technologies) was a kind gift of Dr S J Levine (NIH, Bethesda, USA). The p.E308D and p.A397K variants were introduced into the human GPR101 wt template using the QuikChange Lightning site-directed mutagenesis kit (210518-5, Agilent Technologies), following the manufacturer's protocol. The empty pCMV-XL5 and pcDNA3.1/V5-His TOPO vectors were used as negative controls, accordingly. 24 h after transfection supernatants were collected and GH secretion was measured using the Rat/Mouse Growth Hormone ELISA kit (EZRMGH-45K, EMD Millipore) following the manufacturer's protocol. Absorbance was read at 450 nm and 590 nm using a FLUOSTAR® Omega microplate reader (BMG LABTECH). GH secretion values (expressed in ng/ml) were normalized either on protein content or on O.D. values obtained for the same samples from cell proliferation experiments (see section below).

Cell Proliferation after ARHGEF6, RBMX, and GPR101 Over-Expression

GH3 cells were seeded in 96-well plates at a density of $2 \times 10^4$ cells/well. After 24 h, cells were starved with DMEM without serum for 16 h and then transfected with LIPO-FECTAMINE® 2000 (Life Technologies) according to the manufacturer's protocol, using OPTI-MEM® I Reduced Serum Medium (Life Technologies) and 125 ng of each vector (human WT ARHGEF6, WT RBMX, WT GPR101, p.E308D GPR101, and p.A397K GPR101), alone or in combination. The empty pCMV-XL5 and pcDNA3.1/V5-His TOPO vectors were used as negative controls. 24 h after transfection cell viability was assessed with the VYBRANT® MIT cell proliferation assay (Life Technologies) following the manufacturer's protocol. Briefly, cells were incubated for 4 h at 37° C. with MTT solution and were then lysed with Dimethyl sulfoxide (DMSO). Absorbance was read at 540 nm using a FLUOSTAR® Omega microplate reader (BMG LABTECH).

Results

The three human genes that were expressed in the pituitary tumors (ARHGEF6, RBMX, and GPR101) were transiently over-expressed in the GH3 mammosomatotroph cell line. None of the over-expressed human WT proteins significantly affected cell proliferation or GH secretion when singularly transfected compared to cells transfected with the corresponding empty vector. When human GPR101 was overexpressed together with either or both human ARHGEF6 and human RBMX, a synergistic effect was shown on cell proliferation but not on GH secretion.

GPR101 Over-expression Analysis in Transfected GH3 Cells

GH3 cells transiently transfected with the human WT and mutant GPR101 were analyzed both at the mRNA and protein level for the achieved levels of expression of the receptor. Human GPR101 expression levels are comparable to those observed in the patients with Xq26.3 microduplications.

Example 10: Use of a Reporter Assay to Monitor cAMP Levels after Over-expression of WT and Mutant GPR101 Constructs GH3 cells were seeded in 12-well plates at a density of $2 \times 10^5$ cells/well. After 24 h, cells were starved with DMEM without serum for 16 h and then transfected with LIPO-FECTAMINE® 2000 (11668030, Life Technologies) according to the manufacturer's protocol, using OPTI-MEM® I Reduced Serum Medium (31985-070, Life Technologies), 1 µg of each GPR101 vector (human WT GPR101, p.E308D GPR101, and p.A397K GPR101), 800 ng of pGL4.29[luc2P/CRE/Hygro] vector containing a cAMP response element (CRE) that drives the transcription of the luciferase reporter gene (Promega), and 40 ng of the Renilla vector (pRL-SV40, Promega). The empty pCMV-XL5 vector was used as negative control. 24 h after transfection, a subset of cells was treated with 10 µM forskolin (F6886, Sigma-Aldrich) for 1 h and then lysed. Firefly and Renilla luciferase activities were measured consecutively in the same sample using the DUAL-LUCIFERASE® Reporter Assay System (E1910, Promega) following the manufacturer's protocol. Ratios of Firefly vs. Renilla luminescence signals, serving as a measure for reporter activity normalized for transfection efficiency, were measured using a FLUOSTAR® Omega microplate reader (BMG LABTECH). The results are summarized in FIG. 1F. The figure shows activation of DNA sequences called cyclic AMP response elements (CRE) in rat GH3 cells transfected with mutant (p.E308D and p.A397K) and nonmutant GPR101 constructs. Values for cells transfected with empty (control) vector were set at 1. Also shown are values for untreated cells (vehicle) and forskolin (which increases CRE activation). Like the construct containing the non-mutant receptor, the two mutant constructs resulted in increased cAMP signaling in GH3 cells in an in vitro reporter assay, both at baseline and in the presence of forskolin (10 µM), a direct stimulator of adenylyl cyclase.

Statistical Analysis

Statistical analysis was performed with StatsDirect software (Addison-Wesley-Longman, Cambridge, UK).

Data are presented as the mean±standard deviation (SD) of two to five independent experiments, each performed at least in triplicate. Comparisons were calculated using a two-tailed Student's t test for unpaired data and the Kmuskal-Wallis test followed by the Conover-Inman test, as appropriate. A Chi-square test was used to compare the allelic frequencies of the different genes in patients and controls. The data were considered to be significant when $P<0.05$.

Example 11: Case Report of a Female Sporadic X-LAG Patient

X-linked acrogigantism (X-LAG) syndrome is a of inheritable pituitary gigantism that begins in early childhood and is usually associated with very elevated growth hormone (GH) and prolactin secretion by mixed pituitary adenomas. Microduplications on chromosome Xq26.3 that include the gene GPR101 underlie the genetic etiology of X-LAG syndrome. In individual cases random GH-releasing hormone (GHRH) levels have been elevated.

A series of hormonal profiles were performed in a young female sporadic X-LAG patient and subsequently undertook in vitro studies of primary pituitary tumor culture following a neurosurgical resection.

The patient was a 2-year-old female with no family history of growth disorders. The patient was born at 35.5 weeks gestation and had a birth weight of 2306 g and a birth length of 44.5 cm, which were both below the 3rd percentile. Beginning from 2 months of age the patient began to grow excessively in terms of length and weight, exceeding the 97$^{th}$ percentile of her growth charts by the ages of 12 and 14 months, respectively. The patient was diagnosed with marked GH, IGF-1 and prolactin excess and a pituitary MRI demonstrated a large, uniform sellar lesion (17×8×8 mm) with suprasellar extension. A random level of GHRH was raised, although no potential ectopic sources were identified. Treatment with octreotide (150 mcg sc t.i.d.) and cabergoline (0.5 mg/week) was initiated, but IGF-1 levels remained consistently elevated. The patient was diagnosed with X-LAG syndrome based on an array CGH study that showed a microduplication on chromosome Xq26.3 that was confirmed by fluorescent in situ hybridization studies. As chronic treatment with somatostatin analogs and dopamine agonists for 12 months had no effect on the patient's excessive growth and her pituitary lesion began impinging on the optic chiasm, the patient was referred for neurosurgical treatment.

At transsphenoidal surgery, a gross total resection of the anterior pituitary was performed. Histology revealed a densely cellular tissue specimen comprised of cords of polymorphic cells with abundant cytoplasm (some acidophilic, some chromophobic) and rounded nuclei. Some nuclear atypia was seen and some mitotic figures were seen. Small calcifications were identified but no necrotic foci were seen. Silver staining demonstrated pituitary hyperplasia with widening of the pituitary acini, which was accompanied by focal loss of acinar structure. Immunohistochemistry revealed widespread positivity for GH and prolactin throughout the lesion. Staining for ACTH and TSH was limited to the periphery of the resected tissue and rare cells disseminated within the lesion (LH staining was very rare and FSH staining was absent). Nuclear positivity for p53 was focally highly intense in some cells within the lesion and the Ki67 index was elevated at 5%. CAM 5.2 staining revealed cytoplasmic peri-nuclear and dot-like positivity patterns. The overall pathological result was determined to be an atypical mixed GH/prolactin adenoma associated with anterior hyperplasia.

Postoperatively the patient had cortisol and thyroid deficiencies and diabetes insipidus, which all replaced. Postoperative hormonal levels revealed that GH, IGF-1 and prolactin were in the normal range, and remained so after 6 months' follow-up. The increased growth of the patient has halted.

Example 12: Dynamic Hormone Profiles

Figure 2A:
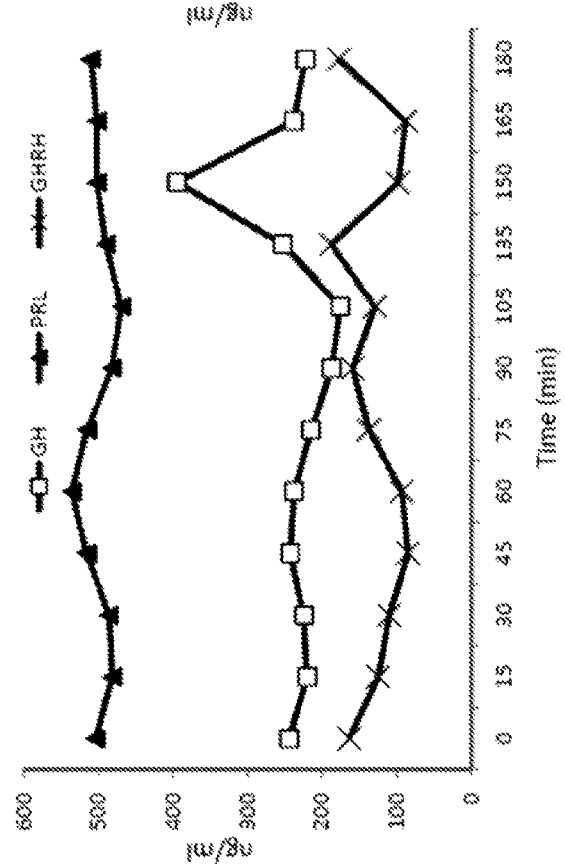

In respect to the case report described in Example 11 pre-operatively a series of dynamic pituitary hormone tests were performed, including a 180 minute test for GH, prolactin and GHRH pulsatility, a GnRH test (25 µg IV GnRH (HRF-AYERST) to study prolactin, GH and GHRH (0, 15, 30 and 90 minutes) and a TRH test (125 µg IV) with measurements of prolactin, GH and GHRH (0, 15, 30 and 90 minutes). These were all performed in the immediate pre-operative period after washout of octreotide (48 hrs.) and cabergoline (24 hrs.). The pulsatility study (FIG. 2A) demonstrated markedly raised levels of GH and PRL throughout and all GHRH levels were elevated at all study time points. Fluctuations in elevated GHRH levels also occurred, and these were partially but not completely in phase with alterations in GH. While the elevated prolactin levels varied by less than +7% from baseline throughout the study, changes in GH levels were more marked (−23.6% to +61.5%).

Figure 2C:
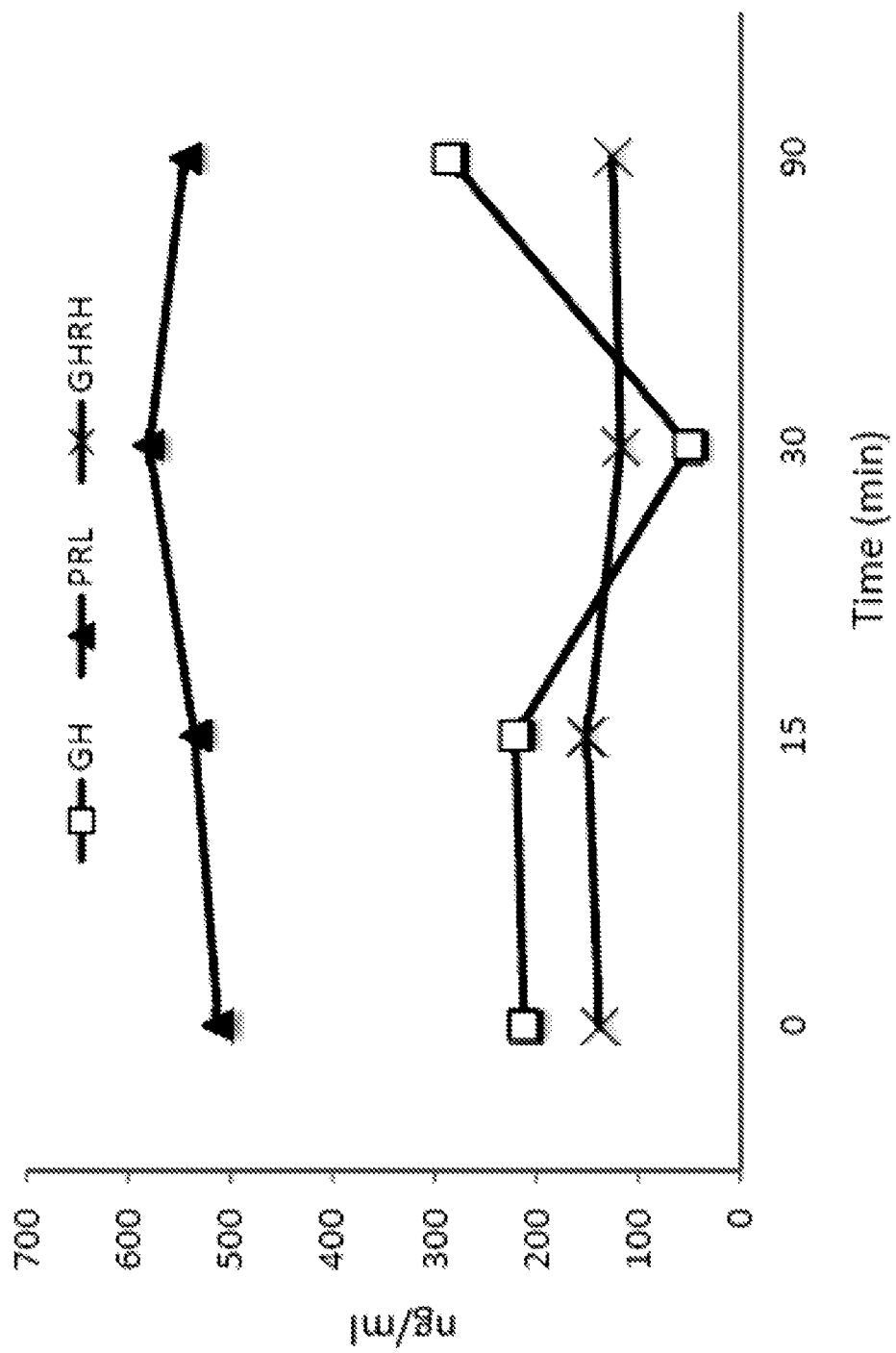
Figure 3B:
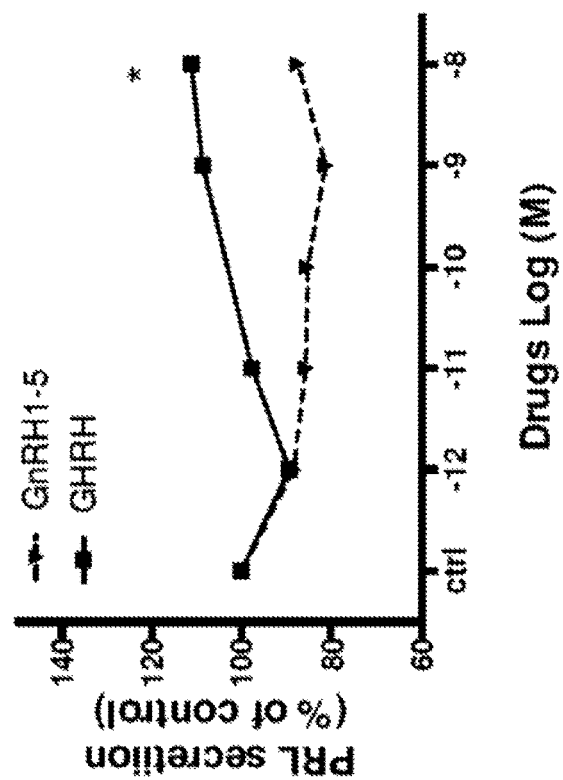
FIGS. 3A-3D shows the in vitro dose-effect on GH (A, C) and PRL (B, D) secretion in somatotroph cells after overnight incubation with (A,B) GHRH, GnRH1-5, (C,D) octreotide (OCT) cabergoline (CAB) or pasireotide (PAS). The results are expressed as the mean percentage of PRL or GH change compared to the values of control wells (ctrl). *: $p<0.05$.
Figure 3A:
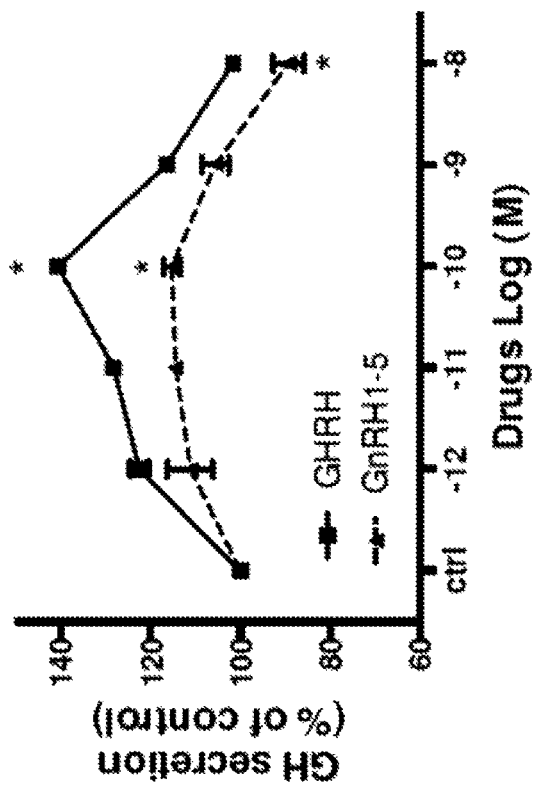
Figure 3D:
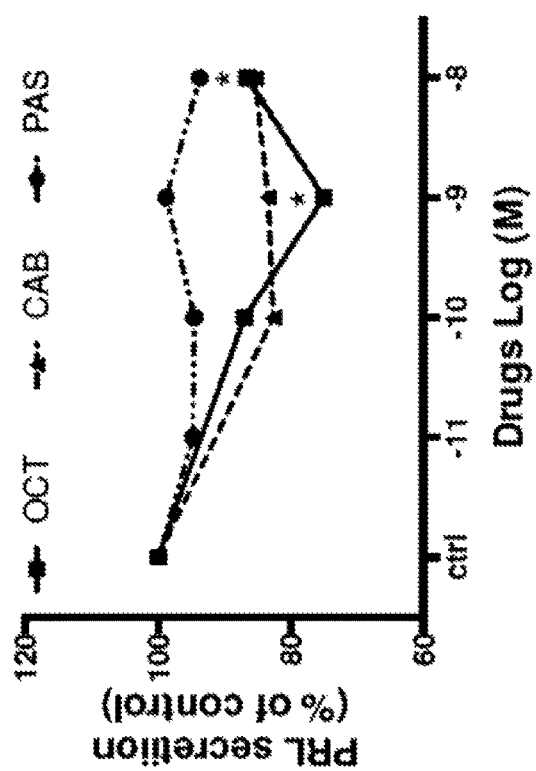
Figure 3C:
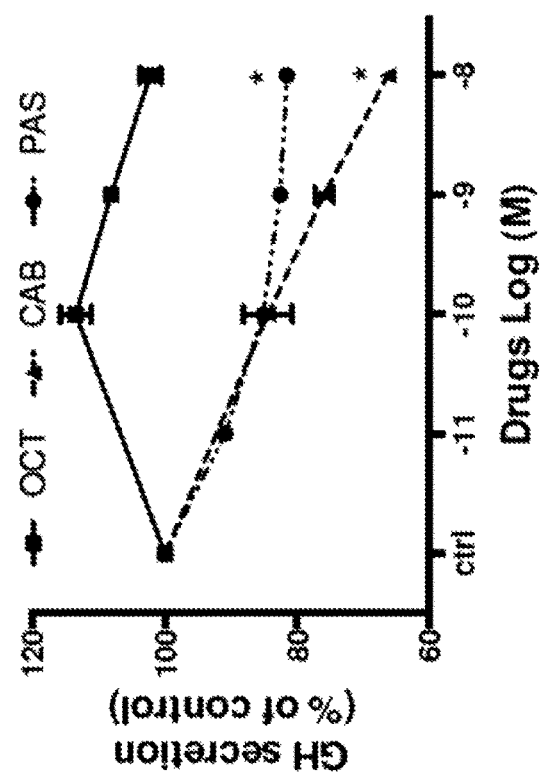

A TRH test (FIG. 2B) led to a paradoxical rise in GH that was accompanied by the expected rise in prolactin. Following GnRH administration (FIG. 2C), the grossly elevated baseline level of GH (212 ng/mL) decreased to 50 ng/mL. Again, the GHRH level was also elevated at baseline (138 pg/mL) and remained elevated throughout.

Example 13: Cell Culture

A surgical sample of the human pituitary adenoma of the patient mentioned in example 11 in Dulbecco's modified Eagle's medium (DMEM) was dissociated mechanically and enzymatically as described by Jaquet et al. (Hormonal regulation of prolactin release by human prolactinoma cells cultured in serum-free conditions. *Horm Res* 22 153-163, 1985). A sample of the medium in the postoperative sample was retained before further preparation. A total of 50,000 tumor cells per well were plated in 24 well plates coated with extracellular matrix from bovine endothelial corneal cells required for cell adhesion. The cells were cultured in DMEM depleted of L-Valine (D-Valine-DMEM) to block fibroblast proliferation, supplemented with 10% fetal calf serum, penicillin (100 U/ml), streptomycin (100 µg/ml), and glutamine (100 U/ml) at 37° C. in a water-saturated atmosphere containing 7% $CO_2$. After 48 h, culture medium was changed to D-Valine DMEM containing 1% ITS (Insulin Transferin Selenium) and 1% fetal calf serum for another 48 h. Cells were incubated with drugs at a range of concentrations ($10^{-12}$-$10^{-7}$ mol/L) for 16 h (overnight). All the experiments were performed in triplicate. The medium was collected and stored frozen for GH and PRL measurements.

Pharmacological Compounds

The somatostatin analogs (SSAs), octreotide and pasireotide were purchased from Novartis (Basel, Switzerland), Forskolin was obtained from Sigma-Aldrich (St. Quentin Fallavier, France), Cabergoline was obtained from Pfizer (Pharmacia & Upjohn Kalamazoo, USA), MK-0677 (ghrelin analog) was obtained from Europeptide, Argenteuil France, and MSP (ghrelin receptor-GHS-R inverse agonist) came from Polypeptide Laboratories (Strasbourg, France). The GHRH receptor antagonist, acetyl-(D-Arg$^2$)-GHRH(1-29) amide, and GnRH$_{1-5}$ were obtained from Bachem, Europe.

Hormonal Assays

GH secretion by the primary culture cells was quantified using the ALPHALISA® human growth hormone GH kit (Perkin Elmer USA). Prolactin levels were measured in culture medium using a commercial IRMA kit (PRL IRMA Kit-Beckman Coulter Immunotech, Marseille, France). Human GHRH concentrations in plasma were measured using an in-house double-antibody radio-immunoassay as described previously and using a standard solution of Stimu-GH 50 µg (Ferring) and the matrix was non-used culture medium (Girard et al.; *Eur. J. Clin. Pharmacol.*, 32, 507-513, 1987).

Cell Culture Experiments

Following 96 h (day 4) of culture of the pituitary surgical sample in FCS and before pharmacological incubation studies, the GHRH concentration was 0.3 ng/50,000 cells. In 1% FCS and ITS, the 24 h secretion for 50,000 cells was 40 ng/ml for GH and 300 ng/ml for prolactin indicating that the tumor cells were actively producing hormone. The GHRH concentration was below the lower limit of the assay (<62 pg/mL) under these same experimental conditions.

As shown in FIG. 3, basal GH secretion was further stimulated by incubation with GHRH reaching a peak at a GHRH concentration of $10^{-10}$M (+41±0.4%). In contrast, the putative GPR101 agonist, GnRH1-5, had little effect on GH across the dose range studied (+15±1.5% at $10^{-10}$ M). Prolactin secretion was slightly stimulated by GHRH, (+11±0.4% at $10^{-8}$M). GnRH1-5 did not stimulate prolactin release.

Figure 5B:
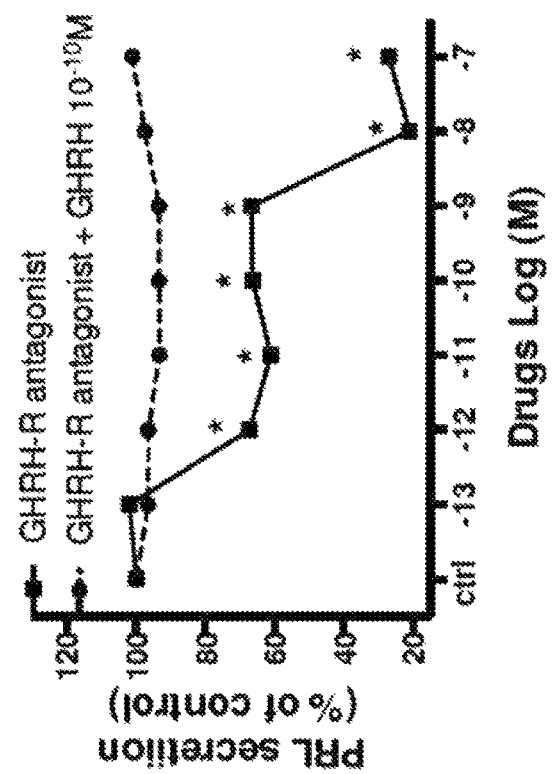
FIGS. 5A-5B show the in vitro dose-effect on GH (A) and PRL (B) secretion in somatotroph cells after overnight incubation with GHRH-R antagonist, with or without GHRH at $10^{-10}$ M. The results are expressed as the mean percentage of PRL or GH change compared to the values of control wells (ctrl). *: $p<0.05$.
Figure 5A:
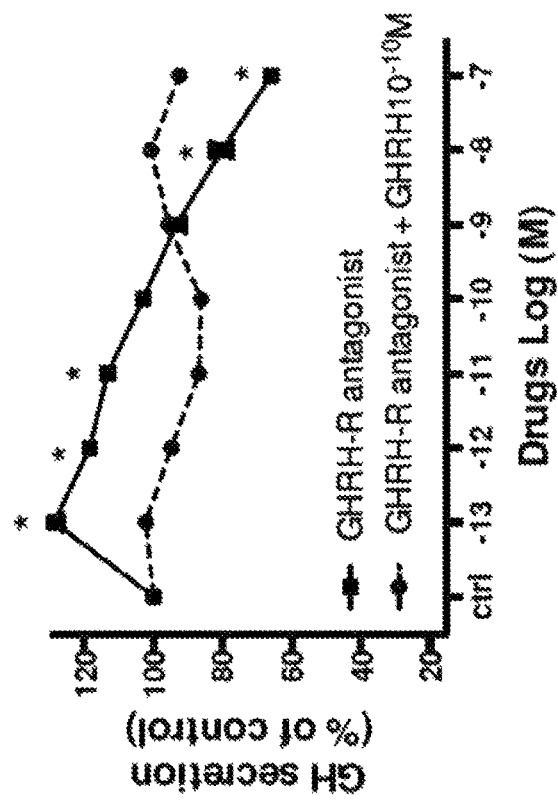

Then the effect of a GHRH receptor antagonist, acetyl-(D-Arg$^2$)-GHRH (1-29) amide on GH and prolactin secretion was studied. There was an initial stimulatory effect of the GHRH-receptor antagonist on GH secretion at $10^{-13}$ M to $10^{-11}$M (+18±0.8% and +13±1.9% respectively). This was followed by a dose dependent inhibition of GH secretion, reducing GH secretion to approximately −34±1.9% of controls at the highest GHRH-receptor antagonist dose studied. Interestingly, incubation with the GHRH receptor antagonist also markedly decreased prolactin secretion, −73±0.1%. at a concentration of $10^{-8}$ M. Co-incubation of GHRH ($10^{-10}$M) with the GHRH antagonist led to complete abolition of the GH and PRL responses to GHRH antagonist. The results are summarized in FIG. 5 which shows the in vitro dose-effect on GH (A) and PRL (B) secretion in somatotroph cells after overnight incubation with GHRH-R antagonist (acetyl-(D-Arg$^2$)-GHRH (1-29) amide), with or without GHRH at $10^{-10}$ M. The results are expressed as the mean percentage of PRL or GH change compared to the values of control wells (ctrl).

When tumor cells were incubated with the SSTR2-specific somatostatin analog, octreotide, no inhibition in GH secretion was seen, while the prolactin decrease was −26±0.03% at $10^{-9}$M. In contrast, following incubation with pasireotide, a multi-somatostatin receptor agonist, a decrease in GH secretion was seen, reaching a maximum inhibition at $10^{-8}$M (−18±0.6%) (pasireotide had no effect on prolactin secretion in these tumor cells). The D2-receptor agonist, cabergoline, displayed stronger inhibition than either somatostatin analog on GH secretion (−32±0.8% at $10^{-8}$M), but the inhibition of prolactin was less (−15±0.04%). The results are summarized in FIG. 3 which shows the in vitro dose-effect on GH (A, C) and PRL (B, D) secretion in somatotroph cells after overnight incubation with (A,B) GHRH, GnRH1-5, (C,D) octreotide (OCT) cabergoline (CAB) or pasireotide (PAS). The results are expressed as the mean percentage of PRL or GH change compared to the values of control wells (ctrl).

Figure 4A:
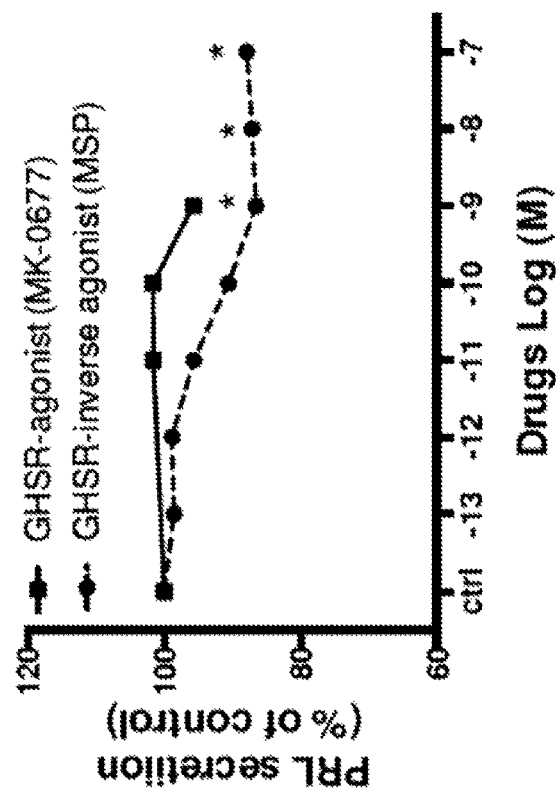
FIGS. 4A-4B show the in vitro dose-effect on GH (A) and PRL (B) secretion in somatotroph cells after overnight incubation with GHSR agonist (MK-0677) or GHSR-inverse agonist (MSP). The results are expressed as the mean percentage of PRL or GH change compared to the values of control wells (ctrl). *: $p<0.05$.
Figure 4B:
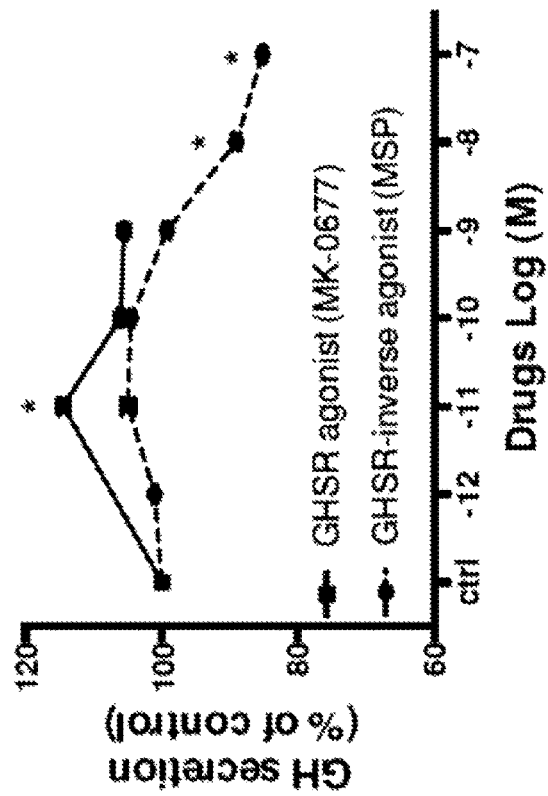

FIG. 4 shows the effects of incubation with a ghrelin analog, MK-0677, and the inverse agonist of the ghrelin receptor, MSP. MK-0677 had a minor stimulatory effect on GH secretion as compared with control (+15±0.5%), while no effect on prolactin secretion occurred. MSP did however decrease GH and PRL secretion by −24%±0.3% and −12±0.08%, respectively, as compared with controls.

Example 14: cAMP Assay

Following the pharmacological co-incubation studies described in Example 13 the response of the tumor cells in terms of cAMP production was assessed. The cells from tumor were seeded into 24-well plates ($4\times10^4$ cells/well). After 24 h in culture, the cAMP concentration was determined using the HTRF-cAMP Femto Kit (CisBio International, Bagnols-sur-Cèze, France), as described previously Cuny et al. (*Mol Cell Endocrinol* 355, 106-113, 2012). According to the manufacturer's protocol, the cells were detached using trypsin, seeded onto 96-well plates in suspension, and incubated at 37° C. for 3 h in the presence of forskolin. The HTRF assay reagents were then added directly into the 96-well plates. As compared with controls, forskolin-treated ($10^{-6}$M) cells exhibited a strong (+396±1.9%) rise in cAMP production.

Statistical Analysis

Data are expressed as mean±SEM. The statistical tests used were the non-parametric paired Wilcoxon and non-paired Mann-Whitney tests. Significance was set at $p \leq 0.05$.

It will be apparent that the precise details of the methods or compositions described may be varied or modified without departing from the spirit of the described invention. We claim all such modifications and variations that fall within the scope and spirit of the claims below.

The invention claimed is:

1. A method for increasing hormone production from the hypothalamus and pituitary gland in a subject, comprising administering to the subject an effective amount of a GPR101 agonist, or a GPR101 protein, thereby increasing hormone production from the hypothalamus and pituitary gland, wherein said subject has a disease of hypopituitarism and low levels of pituitary hormone secretion.

2. The method of claim 1, wherein said subject is a human.

3. The method of claim 1, wherein said subject is a non-human animal.

4. A method for increasing hormone production from the hypothalamus and pituitary gland in a subject, comprising administering to the subject an effective amount of a GPR101 agonist, or a GPR101 protein, thereby increasing hormone production from the hypothalamus and pituitary gland, wherein said subject has a disease of dwarfism or short stature due to growth hormone deficiency.

5. The method of claim 4, wherein the method increases the growth velocity of the subject.

6. The method of claim 4, wherein said subject is a human.

7. A method for reducing hormone secretion from the hypothalamus and pituitary gland in a subject comprising administering to the subject an effective amount of a GPR101 antagonist, thereby reducing hormone secretion from the hypothalamus and pituitary gland in the subject, wherein the subject has gigantism.

8. The method of claim 7, wherein said subject is a human.

9. A method of treating a subject with gigantism, comprising:
selecting a subject with gigantism, and
administering to the subject a therapeutically effective amount of a GPR101 antagonist, thereby reducing growth hormone secretion and treating the gigantism in the subject.

10. The method of claim 9, wherein the GPR101 antagonist is an inhibitory ribonucleic acid (RNA) molecule.

11. The method of claim 9, wherein the subject has a microduplication in chromosome Xq26.3 comprising the orphan G-protein coupled receptor (GPCR) gene GPR101.

12. The method of claim 9, wherein said subject is a human.

* * * * *